United States Patent [19] [11] 4,035,414
Gandolfi et al. [45] July 12, 1977

[54] PROSTANOIC ACID DERIVATIVES
[75] Inventors: Carmelo Gandolfi; Gianfederico Doria, both of Milan; Pietro Gaio, Lamon, Belluno, all of Italy
[73] Assignee: Carlo Erba S.P.A., Milan, Italy
[21] Appl. No.: 631,656
[22] Filed: Nov. 13, 1975

Related U.S. Application Data
[62] Division of Ser. No. 346,249, March 30, 1973, Pat. No. 3,935,254.

[30] Foreign Application Priority Data
Apr. 13, 1972  Italy ................................ 23063/72
Apr. 28, 1972  Italy ................................ 23662/72

[51] Int. Cl.$^2$ ..................................... C07C 177/00
[52] U.S. Cl. ........................ 260/514 D; 260/468 D
[58] Field of Search .................... 260/468 D, 574 D

[56] References Cited
PUBLICATIONS
Fried, et al., J. Med. Chem. 16, 429 (1973).

Primary Examiner—Robert Gerstl
Attorney, Agent, or Firm—Cushman, Darby & Cushman

[57] ABSTRACT
8,12-diso-14-chloro $PGE_2$ and $PGF_2$ and 8,12-diso-prosten-ynoic acids have been prepared.

22 Claims, No Drawings

PROSTANOIC ACID DERIVATIVES

CROSS-REFERENCE TO RELATED APPLICATIONS

This is a division of our copending application Ser. No. 346,249 filed Mar. 30, 1973, now U.S. Pat. No. 3,935,254.

This invention relates to prestanoic acid derivatives, to processes for making them, to pharmaceutical compositions containing them and to novel intermediates useful in the processes.

The natural prostaglandins are C-20 unsaturated, non-aromatic fatty hydroxylic carboxylic acids in which $C_8$ and $C_{12}$ are linked to form a five-membered ring. The basic carbon skeleton of prostanoic acid has the following structure:

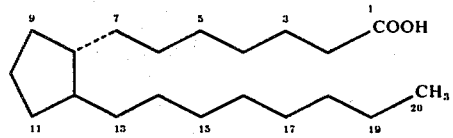

In the body, prostaglandins are synthesized from C-20 essential fatty acids by a microsomal enzymatic system.

The natural prostaglandins are known to have various physiological properties, i.e. hypertensive, hypotensive and smooth muscle stimulating activity. They also inhibit and reverse blood platelet adhesiveness and aggregation, which is the initial stage of thrombosis.

In general, the effects of prostaglandins are based on regulating the activity of smooth muscle, blood flow and secretion (including some endocrine gland secretions). Through these actions, they are able to affect many aspects of human physiology: in particular, they can be useful in the prevention of peptic ulcers, asthmatic access, hypertension, nasal congestion, as agents for abortion, as agents for inducing menstruation and the impediment of the implantation of a fertilized oyum, and furthermore prostaglandins have been used in parturition to facilitate childbearing labour. Natural prostaglandins are, however, rapidly converted in the body to pharmacologically inactive metabolites; their short half life (about 10 minutes) is a hindrance to the use of natural prostaglandins as therapeutic agents. Dehydrogenation of the allylic hydroxy function at C-15 which is present in all the naturally occurring prostaglandins, by '5-hydroxy-prostaglandin dehydrogenases (NAD-dependent enzymes), is the first and more important metabolic step:

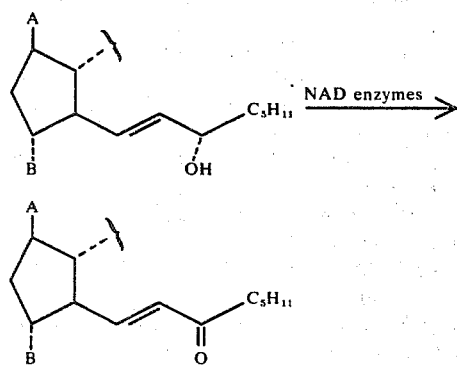

This first degradation step, involving the conversion into $\Delta^{13(14)}$-15-keto prostaglandins, transforms the prostaglandins into pharmacologically inactive metabolites [Anggard E., Acta Physiol. Scand., 66, 509 (1966); Kloeze J., Biochim. Biophys. Acta, 187, 285 (1969)].

We have therefore synthetised, and they are object of this invention, new prostaglandin type compounds, wherein some molecular modifications are present, in order to obtain a favourable effect on biological parameters and to maintain a prostaglandin-like activity.

More particularly, the invention provides pure optically active or racemic prostanoic acid derivatives, all of which have a reduced metabolic degradation rate compared with natural prostaglandins, thus allowing an efficient therrapeutic action at lower dosages.

The prostanoic acid derivatives of this invention can be used in the same applications as the natural prostaglandins discussed hereinbefore.

The compounds of the invention are those of general formulas

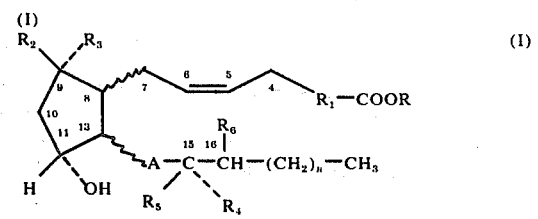

and (II)

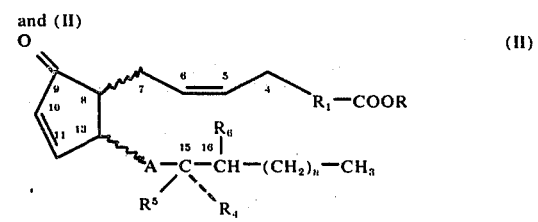

and the racemates thereof, wherein R is a hydrogen atom, a pharmaceutically acceptable cation or a $C_{1-12}$ alkyl group; $R_1$ is $-CH_2CH_2-$, $-OCH_2-$, $-SCH_2-$, $-CH=CH-$ or $-C\equiv C-$; one of $R_2$ and $R_3$ is a hydrogen atom and the other is a hydroxy group or $R_2$ and $R_3$ together form an oxo group; A is

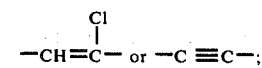

one of $R_4$ and $R_5$ is a hydrogen atom and the other is a hydroxy group; $R_6$ is a hydrogen atom or a $C_{1-4}$ alkyl group; $n$ is 3 or 4; and wherein the chains bound to the carbon atoms in the 8-position and in the 12-position have the trans-configuration. The double bond in the 5(6)-position is a cis-double bond. In the group

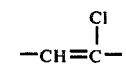

the double bond is a trans-double bond. When $R_1$ is $-CH=CH-$, it may be either cis—$CH=CH-$ or trans—$CH=CH-$.

In the formulae of this specification the broken lines indicate that the substituents are in the α-configuration, i.e. are below the plane of the ring or, respectively, of the chain, while the wavy line attachment (⌇) indicates that the groups may be either in the α-configuration, i.e. below the plane of the ring, or in the β-configuration, i.e. above the plane of the ring.

As stated above, the chains bound to the carbon atoms in the 8-position and in the 12-position must have the trans-configuration, i.e. these chains cannot be contemporaneously both in the α-configuration or both in the β-configuration, but, when one of them is in the α-configuration, the other is in the β-configuration and viceversa. As is evident from formulae (1) and (11), the hydroxy group linked to the carbon atom in the 15-position may be either in the α-configuration

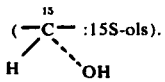

or in the β-configuration

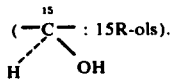

As stated above, object of the invention are either optically active compounds or racemic compounds.

Compounds of the invention are therefore either optically active compounds having the general formulas

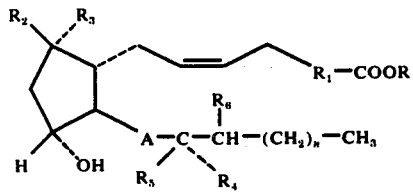

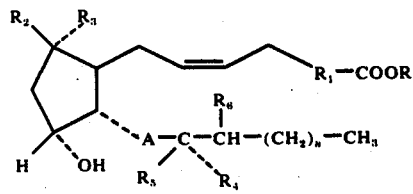

and their racemates,
or optically active compounds having the general formulas

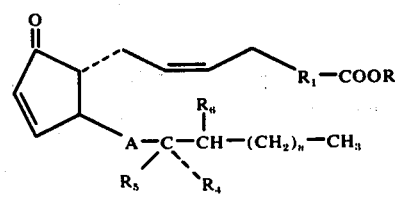

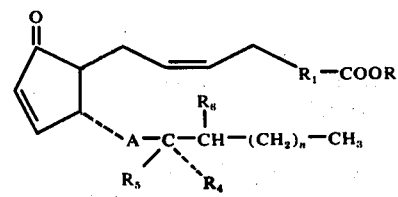

and their racemates. Preferred compounds of the invention are those of general formula (1) wherein $R_1$ is —$CH_2CH_2$— or —$OCH_2$—.

Examples of specific compounds of the invention are:

5c,13t-14-chloro-9α,11α,15S-trihydroxy-prostadienoic acid;
5c,13t-14-chloro-9α,11α,15S-trihydroxy-8,12-diiso-prostadienoic acid;
5c,13t-14-chloro-9β,11α,15S-trihydroxy-8,12-diiso-prostadienoic acid;
5c,13t-14-chloro-11α,15S-dihydroxy-9-oxo-prostadienoic acid;
5c,13t-14-chloro-15S-hydroxy-9-oxo-prosta-5,10,13-trienoic acid;
5c,13t-14-chloro-11α,15S-dihydroxy-9-oxo-8,12-diiso-prostadienoic acid;
5c,13t-14-chloro-15S-hydroxy-9-oxo-8,12-diiso-prosta-5,10,13-trienoic acid;
5c-9α,11α,15S-trihydroxy-prosten-13-ynoic acid;
5c-16-methyl-9α,11α,15S-trihydroxy-prosten-13-ynoic acid;
5c-9α,11α,15S-trihydroxy-20ω-homo-prosten-13-ynoic acid;
5c-9α,11α,15S-trihydroxy-3-oxa-prosten-13-ynoic acid;
5c-9α,11α,15R-trihydroxy-prosten-13-ynoic acid;
5c-9α,11α,15S-trihydroxy-8,12-diiso-prosten-13-ynoic acid;
5c-16methyl-9α,11α,15S-trihydroxy-8,12-diiso-prosten-13-ynoic acid;
5c-9α,11α,15S-trihydroxy-20ω-homo-8,12-diiso-prosten-13-ynoic acid;
5c-9α,11α,15S-trihydroxy-3-oxa-8,12-diiso-prosten-13-ynoic acid;
5c-9α,11α,15S-trihydroxy-8,12-diiso-prosten-13-ynoic acid;
5c-11α,15S-dihydroxy-9-oxo-prosten-13-ynoic acid;
5c-11α,15R-dihydroxy-9-oxo-prosten-13-ynoic acid;
5c-16-methyl-11α,15S-dihydroxy-9-oxo-prosten-13-ynoic acid;
5c-16-methyl-11α,15R-dihydroxy-9-oxo-prosten-13-ynoic acid;
5c-11α,15S-dihydroxy-9-oxo-20ω-homo-prosten-13-ynoic acid;
5c-11α,15S-dihydroxy-9-oxo-20ω-homo-prosten-13-ynoic acid;
5c-11α,15S-dihydroxy-9-oxo-3-oxa-prosten-13-ynoic acid;
5c-11α,15R-dihydroxy-9-oxo-3oxa-prosten-13-ynoic acid;
5c-11α,15S-dihydroxy-9-oxo-8,12-diiso-prosten-13-ynoic acid;
5c-11α,15R-dihydroxy-9-oxo-8,12-diiso-prosten-13-ynoic acid;
5c-16-methyl-11α,15S-dihydroxy-9-oxo-8,12-diiso-prosten-13-ynoic acid;
5c-16-methyl-11α,15R-dihydroxy-9-oxo-8,12-diiso-prosten-13-ynoic acid;
5c-11α,15S-dihydroxy-9-oxo-20ω-homo-8,12-diiso-prosten-13-ynoic acid;
5c-11α,15R-dihydroxy-9-oxo-20ω-homo-8,12-diiso-prosten-13-ynoic acid;
5c-11α,15S-dihydroxy-9-oxo-3oxa-8,12-diiso-prosten-13-ynoic acid;
5c-11α,15R-dihydroxy-9-oxo-3-oxa-8,12-diiso-prosten-13-ynoic acid;
5c-15S-hydroxy-9-oxo-prosta-5,10-dien-13-ynoic acid,
5c-16-methyl-15S-hydroxy-9-oxo-prosta-5,10-dien-13-ynoic acid;

5c-15S-hydroxy-9-oxo-20ω-homo-prosta-5,10-dien-13-ynoic acid;

5c-15S-hydroxy-3-oxa-9-oxo-prosta-5,10-diene-13-ynoic acid;

5c-15S-hydroxy-9-oxo-8,12-diiso-prosta-5,10-dien-13-ynoic acid;

5c-16-methyl-15S-hydroxy-9-oxo-8,12-diiso-prosta-5,10-dien-13-ynoic acid;

5c-15S-hydroxy-9-oxo-20ω-homo-S,12-diiso-prosta-5,10-dien-13-ynoic acid;

5c-15S-hydroxy-9-oxo-3-oxa-8,12-diiso-prosta-5,10-dien-13-ynoic acid;

The ω-homo compounds are those wherein $n$ is 4.

The compounds of general formulas (I) and (II) may be prepared by a process comprising reacting an optically active or racemic compound of general formula (III)

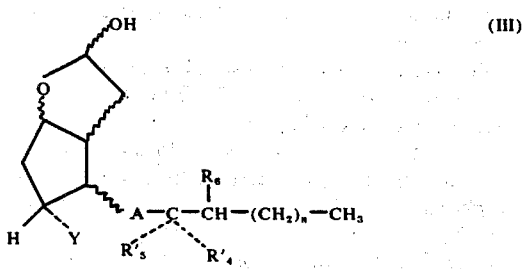

wherein $R_6$, $n$ and A are as defined above, one of $R'_4$ and $R'_5$ is a hydroxy or a known protecting group bound to the chain by an ethercal oxygen atom, and the other is a hydrogen atom, Y is a hydroxy or a known protecting group bound to the ring by an ethereal oxygen atom and wherein the lactolic ring is in the trans-configuration in respect of the hydroxy-aliphatic side chain, with a Wittig reagent comprising the group $-CH_2CH_2-R_1$ $-COOR$, wherein $R_1$ is as defined above and R is a hydrogen atom or a $C_{1-12}$ alkyl group, to give a compound of general formula (IV)

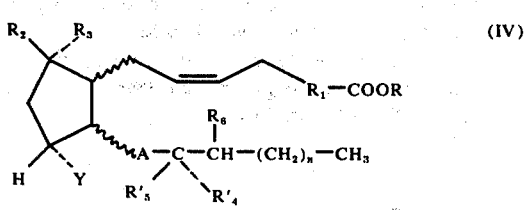

wherein R, $R_1$, Y, A, $R'_4$, $R'_5$, $R_6$ and $n$ are as defined above, and wherein one of $R_2$ and $R_3$ is a hydroxy group and the other is a hydrogen atom, and then deetherifying in the 11-and/or 15-position the compound of formula (IV) wherein Y is a known protecting group as defined above and/or one of $R'_4$ and $R'_5$ is a known protection group as defined above and the other is a hydrogen atom and then, if desired, oxidizing in the 9-position the compound of general formula (IV) wherein Y is a known protecting group as defined above and one of $R'_4$ and $R'_5$ is a known protecting group as defined above and the other is a hydrogen atom, so obtaining a compound of general formula (V)

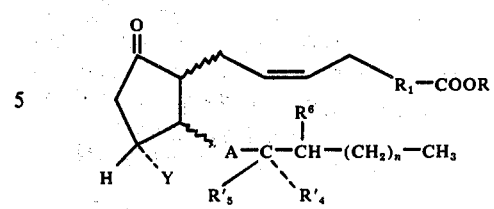

wherein R, $R_1$, A, $R_6$ and $n$ are as defined above, Y is a known protecting group as defined above, and one of $R'_4$ and $R'_5$ is a known protecting group as defined above and the other is a hydrogen atom, which, in turn, may be either directly deetherified in the 11- and 15-positions, to give, according to the reaction conditions used, a compound of general formula (I), wherein $R_2$ and $R_3$ together form an oxo group, or a compound of general formula (II), or reduced in the 9-position to give a mixture of the 9α-and 9β-ols of general formulas (VI) and (VII)

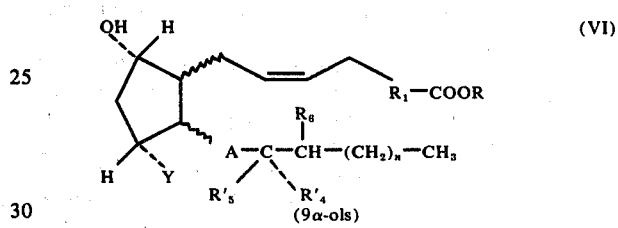

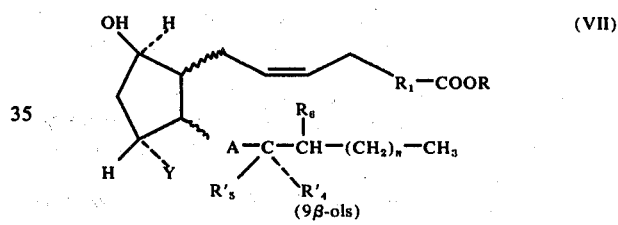

wherein R, $R_1$, A, $R_6$ and $n$ are as defined above, Y is a known protecting group as defined above and one of $R'_4$ and $R'_5$ is a known protecting group as defined above and the other is a hydrogen atom, which mixture is then, in any order, separated and deetherified in the 11- and 15-positions, so obtaining a compound of general formula (I) wherein one of $R_2$ and $R_3$ is a hydroxy group and the other is a hydrogen atom.

Compounds of formula (IV) wherein A is

can be converted into compounds of formula (IV) wherein A is $-C≡C-$. The conversion may be performed, for example, by using an excess of tert-BuOK (e.g. 2.1 to 3 moles) in a suitable organic solvent, for example dimethylsulphoxide. Compounds where R is a hydrogen atom can be esterified or reacted with a pharmaceutical acceptable base, according to the usual methods of organic chemistry, to give compounds wherein R is, respectively, a $C_{1-12}$ alkyl group or a pharmaceutically acceptable cation.

Examples of pharmaceutical acceptable cations are either metallic cations, such as sodium, potassium, calcium, aluminium and the like, or organic amine cations such as, e.g., trialkylamines.

Compounds of formula (1) wherein one of $R_2$ and $R_3$ is a hydrogen atom and the other is a hydroxy group, and wherein R is a $C_{1-12}$ alkyl group, can be hydrolysed to give compounds of formula (I) wherein $R_2$ and $R_3$ have the same meanings and R is a hydrogen atom. The reaction can be performed according to the usual methods of organic chemistry, as is known to those skilled in the art.

Compounds of formula (I) wherein $R_2$ and $R_3$ together form an oxo group and wherein R is a $C_{1-12}$ alkyl group, and compounds of formula (II), wherein R is a $C_{1-12}$ alkyl group, can be hydrolysed to give compounds of formula (1) wherein $R_2$ and $R_3$ together form an oxo group and wherein R is a hydrogen atom or, respectively, to give compounds of formula (II) wherein R is a hydrogen atom by enzymatic way, for example by using yeast esterase. In the compounds (IV) to (VII), which may be either optically active or racemic compounds, the chains attached to the carbon atoms in the β-position and in the 12-position, respectively, are always in the trans-configuration.

As stated above, as starting material of formula (III) may be used either an optically active or a racemic lactol.

In the lactol of formula (III), the two bonds of the lactolic ring indicated by the wavy line attachment ($) are in the cis-configuration, i.e. they are contemporaneously both below the plane of the cyclopentane ring or both above the plane of the cyclopentane ring, while, as stated above, the side chain is in the trans-configuration in respect of the lactolic ring, i.e. it is below the plane of the cyclopentane ring when the lactolic ring is above the plane of the cyclopentane, ring, and viceversa.

The lactolic hydroxy group may be either in the α-configuration, i.e. below the plane of the lactolic ring, or in the β-configuration, i.e. above the plane of the lactolic ring.

The starting material may therefore be either a compound of formula

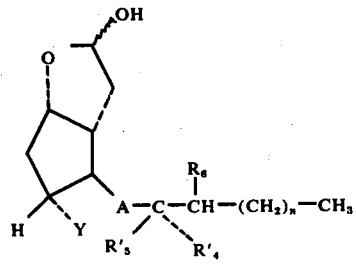

(IIIa)

or a compound of formula

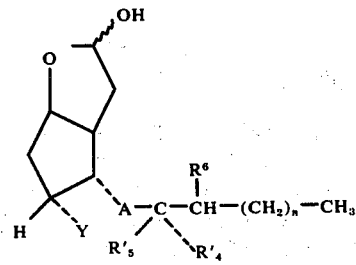

(IIIb)

or a racemate thereof.

When the compound (IIIa) is used as starting material, a compound (IV) is obtained wherein $R_2$ is a hydrogen atom and $R_3$ is a hydroxy group. When the compound (IIIb) is used as starting material, a compound (IV) is obtained wherein $R_2$ is a hydroxy group and $R_3$ is a hydrogen atom.

The known protecting groups (i.e. ether groups) should be convertible to hydroxy groups under mild reaction conditions, e.g. acid hydrolysis. Example are acetalic etners, enolethers and silylethers. The preferred groups are

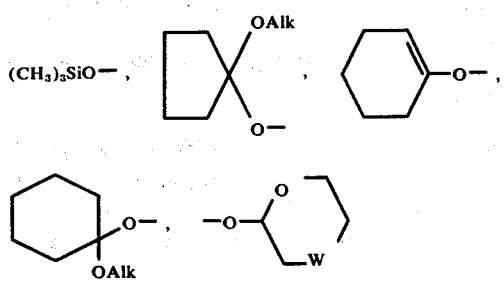

wherein W is —O— and —$CH_2$—, and Alk is a lower alkyl group.

The Witting reaction is suitable carried out using at least one mole, preferably 2–10 moles, of the Witting reagent per mole of lactol.

The reaction is generally performed in an organic solvent, for example, diethylether, hexane, dimethylsulphoxide, tetrahydrofuran, dimethylformamide, hexamethylphosphoramide, in presence of a base, preferably sodium hydride and potassium tert.-butoxide, at 0° C to the reflux temperature of the reaction mixture, preferably at room temperature or below. The reaction can take a few minutes to several days depending on the temperature and concentration of the reaction mixture and the specific Wittig reagent used.

The term "Wittig reagent" includes compounds of general formula $(Aryl)_3 — P^+ — CH_2 — CH_2 — R_1 — COOR\ Hal^-$ wherein Hal is bromo or chloro and R and $R_1$ are as defined above. Other phosphorus derivatives, e.g. the diethyl derivatives, are also included. The preparation of these reagents is discussed in detail by Tripett, Quart. Rev. 1963 XVII, No. 4, 406.

According to the reaction conditions used, it is possible to obtain, starting from a compound of general formula (III) wherein A, is

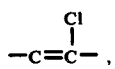

either a compound of formula (IV) wherein A is C≡C-, or a compound of formula (IV) wherein A is

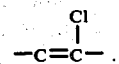

The compound of formula (IV) wherein A is

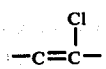

may be, in fact, obtained as the only product by using, for example, 1.5 to 2.5 moles of Wittig reagent per mole of compound (III) and by using reaction times ranging between above 10 minutes and about 30 minutes.

The compound of formula (IV) wherein A is —C≡C— may be, on the contrary, obtained as the only product, by using for example, 1.5 to 2.5 moles of Wittig reagent per mole of compound (III) and by using reaction times ranging between about 2 hours and about 10 hours. Analogously the compound of formula (IV) wherein A is —C≡C— may be obtained by using reaction times of about 30 minutes and at least 5 moles of Wittig reagent per mole of compound (III).

Preferably, in the starting material of formula (III), A is

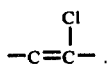

The deetherification of compound (IV) is performed under conditions of mild acid hydrolysis, for example with mono-or poly-carboxy acids e.g. formic, acetic, oxalic, citric and tartaric acid, and in a solvent, for example water, acetone, tetrahydrofuran, dimethoxyethane and lower aliphatic alcohols. Preferably, 0.1N to 0.25N polycarboxylic acid (e.g. oxalic or citric acid) is used in the presence of a convenient low boiling co-solvent which is miscible with water and which can be easily removed in vacuo at the end of the reaction.

The oxidation of the 9-hydroxy group to yield an oxo group may be carried out with for example, Jones reagent.

As stated above, the deetherification of the compound of general formula (V) may give, according to the reaction conditions used, either a compound of general formula (I) wherein $R_2$ and $R_3$ together form an oxo group or a compound of general formula (II).

The compound of formula (I), wherein $R_2$ and $R_3$ together form an oxo group, may be obtained, as the only product, by operating at temperatures ranging between about 25° and between about 40° C, while by operating at higher temperatures, for example at the reflux temperature for about 3 hours, the compound of formula (II) is obtained as the only product. The reduction of the keto group in the 9-position of the compound (V) to give a mixture of the 9α-hydroxy and 9β-hydroxy-11-ethers may be performed for example by using sodium, lithium or zinc borohydride.

This reduction is performed in order to obtain a compound of formula (I) wherein $R_2$ is a hydrogen atom and $R_3$ is a hydroxy group also when the starting material is a lactol of formula (IIIb) and, respectively, in order to obtain a compound of formula (I) wherein $R_2$ is a hydroxy group and $R_3$ is a hydrogen atom also when the starting material is a lactol of formula (IIIa).

The separation of the 9α-hydroxy and 9β-hydroxy-11-ethers from each other and/or from the free 11,15-diols may be carried out for example by chromatographic techniques, preferably column chromatography.

The subsequent deetherification may be performed as described above under conditions of mild acid hydrolysis, for example with oxalic acid in acetone.

The compounds of general formula (II) may be prepared in turn, by means of a multi-step process using as starting material an optically active or racemic lactone of general formula (VIII)

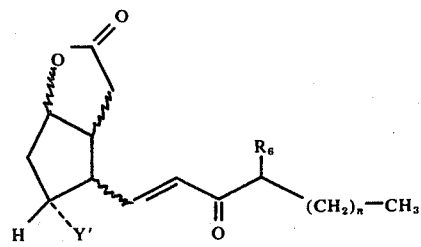

wherein $R_6$ and $n$ are as defined above and $Y'$ is a hydroxy group or an aliphatic, aromatic or cycloaliphatic acyloxy group or a known protecting group bound to the cyclopentane ring by an ethereal oxygen atom and wherein the lactonic ring is in the trans-configuration in respect of the ketoaliphatic side chain.

The lactone used as starting material may therefore be either a compound of formula (VIIIa)

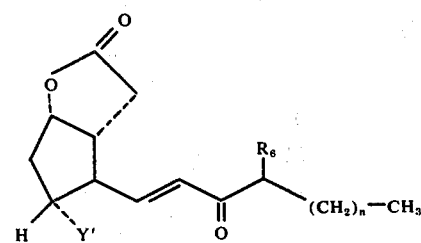

or a compound of formula (VIIIb)

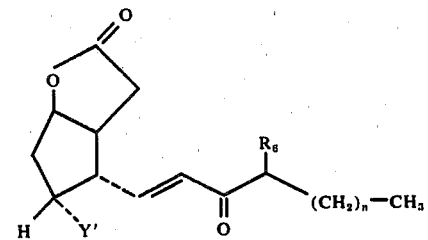

or a racemate thereof.

The compound of formula (VIIIa) may be prepared substantially as described by E. J. Corey et al., Annals of N.Y. Ac. of Sciences, 180, 21 (1971).

The compound of formula (VIIIb) may be prepared substantially by means of a multi-step process using as starting material a pure optically active compound of general formula (A)

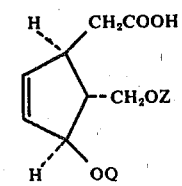

wherein Z is a lower alkyl group, preferably methyl, or an unsubstituted or substituted aralkyl group, preferably benzyl or p-methoxybenzyl, and Q is a hydrogen atom or an aliphatic acyl group. The compound of formula (A) may be prepared by crystallization with optically active bases and acylation by conventional methods, starting from the compound of general formula

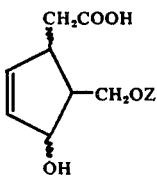

wherein Z is as defined above. This compound is a mixture of both optical antipodes (laevorotatory and dextrorotatory). Its preparation is described by Corey et al., J. Am. Chem. Soc., 1969 91, 5675; ibid. 1971, 93, 1489 and 1491 ibid., 1971, 93, 4326, who however use, in the total synthesis of the naturally occurring prostaglandins, only the dextrorotatory antipode having the absolute formula

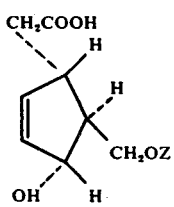

The starting material used in the present invention is the laevorotatory antipode having the absolute formula (A). The multi-step process to obtain the compound of general formula (VIIIb) involves the following steps:

1. Reaction of the compound of formula (A), in the form of a salt with an alkali or alkaline earth metal or an optically active base, with an aqueous solution of potassium triiodide to give a compound of general formula (B)

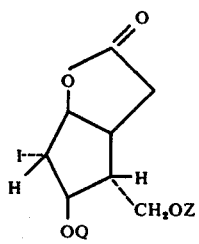

wherein Z and Q are as defined above;

2. Dehalogenation of the compound of formula (B) to give a compound of formula (C)

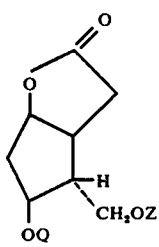

wherein Z and Q are as defined above; if Q is a hydrogen atom, the dehalogenation is preferably performed with a reducing agent, which is preferably tributyl tin hydride in benzene or chromous acetate in thioethanol and dimethylsulphoxide. If Q is an acyl group, the dehalogenation is preferably performed with sodium cyanoborohydride in hexamethylphosphoric triamide;

3. Reaction of the compound of formula (C), after saponification if Q is an acyl group, with a halide of formula $R^aSO_2X$, wherein X is a halogen atom and $R^a$ is an unsubstituted or substituted alkyl or aryl group, to give a compound of general formula (D)

wherein $R^a$ and Z are as defined above; the reaction is suitably performed in presence of a base, preferably pyridine, an alkylpyridine or a trialkylamine;

4. Reaction of a compound of formula (D) with an aliphatic carboxylic acid salt to give a compound of general formula (E)

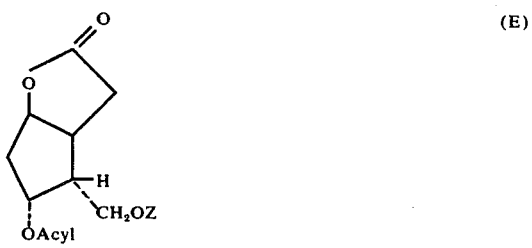

wherein Z is as defined above; the carboxy acid is preferably formic, acetic or propionic acid and the reaction is preferably performed in a solvent, e.g. water, dimethylsulphoxide, dimethylformamide, hexamethyl phosphoric triamide, acetone or 2-butanone or their mixtures. The small amount of the $\Delta^{3(4)}$-lactone which is simultaneously obtained can be easily removed by fractional crystallization or column chromatography;

5. Saponification to yield the 4-ol; the saponification may be performed by conventional methods using an alkali or acid;

6. Esterification of the 4-ol with an aromatic carboxy acid. Esterification is preferably performed with p-phenylbenzoylchloride in pyridine. This esterification involves an aroyl group because the presence of such a group facilitates the subsequent oxidation to an aldehyde and yields a more easily crystallizable product;

7. Deetherification of the compound thus obtained to give a compound of general formula (F)

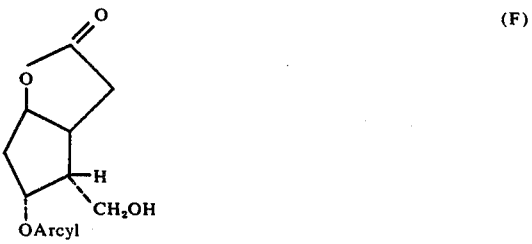

the deetherification is suitably performed using $BBr_3$, $BCl_3$, $(C_6H_5)_3C^+ ClO_4^-$, $(C_6H_5)_3C^+ BF_4^-$ in a suitable solvent, for example methylene chloride, and for the benzyl ethers using reductive cleavage with hydrogen in presence of $PtO_2$ or palladium on carbon as catalyst;

8. Oxidation of the compound of general formula (F) to yield the compounds of general formula (G)

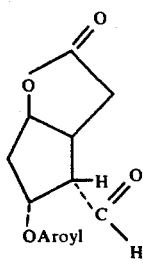

The oxidation may be performed for example in dimethyl sulphoxide using a carbodiimide, for example dicyclohexylcarbodiimide, in presence of a suitable protonating agent, e.g. orthophosphoric acid or pyridine trifluoroacetate, or if desired by means of a modified Collins reagent (Ratcliffe and Rodehorst, 1970 J. Org. Chem. 35, 4000);

9. Reaction of the aldehyde with an alkali or alkaline earth metal salt of a compound of general formula (L)

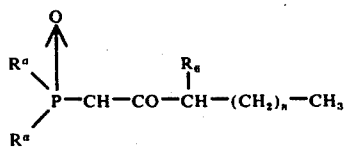

wherein $R^6$, and $n$ are as defined above, and each of the groups $R^a$, which may be the same or different is a lower alkyl group, to give a trans-enone of general formula (VIIIb)

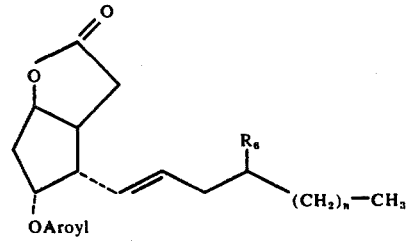

wherein $R^6$, and $n$ are as defined above. The reaction is suitably performed in a solvent which is preferably dry dimethoxyethane, tetrahydrofuran or benzene or their mixtures, and using a suspension of an alkali or alkaline earth metal salt of the compound of general formula (L) in this solvent. The compound of general formula (L) may be prepared by reacting a phosphonate of the formula

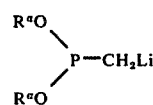

wherein $R^a$, is as defined above, with an ester of formula

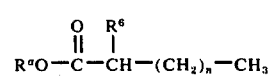

wherein $R^a$, $R^6$ and $n$ are as defined above, according to Corey and Kwiatkowski, 1966, J. Amer. Chem. Soc., 88, 5654.

The racemates may be prepared substantially according to the same methods.

The multi-step process to obtain the compound of general formula (VIII) involves the following steps:
1. reaction of a compound of formula (VIII) with a halogenating agent to give a compound of formula

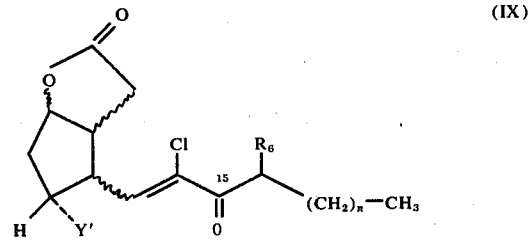

wherein Y′, $R_6$ and $n$ are as defined above. A suitable halogenating agent is, for example, a sulphonylchloride, preferably $SO_2CL_2$: the reaction may be performed in a solvent preferably selected from the group consisting of pyridine, acetone, acetic acid, toluene, diethylether, benzene, water or their mixtures;

2. reduction of the 15-oxo-group (prostaglandin numeration) of the compound of formula (IX) to yield a mixture of the 15S and 15R ols having the formulae

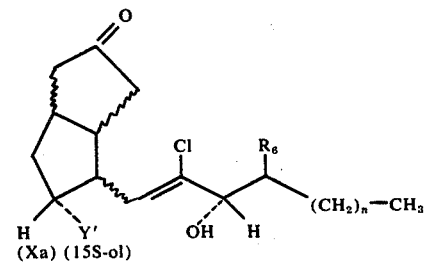

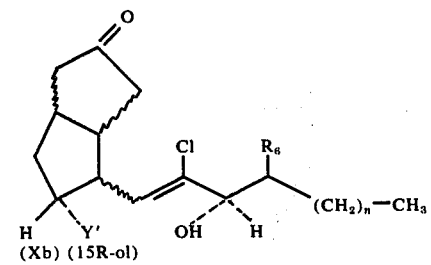

wherein Y′, $R_6$ and $n$ are as defined above, followed by separation of the 15S-ol from the 15R-ol and subsequently, if desired, by dehydrohalogenation of the separated compounds to give a compound of formula (XIa)

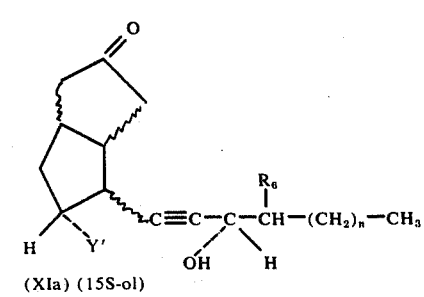

or a compound of formula (XIb)

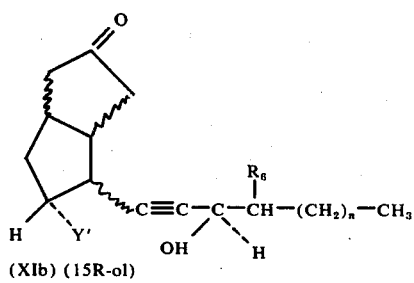

(XIb) (15R-ol)

wherein Y', R$_6$ and n are as defined above;

if desired, the reduction may follow the dehydrohalogenation. The reduction of the 15-oxo group may be suitably performed in an organic solvent, such as acetone, diethylether, dimethoxyethane, dioxan, or benzene and their mixtures, by using sodium borohydride, lithium borohydride or zinc borohydride. The separation of the 15S-ol from the 15R-ol may be performed by chromatography, preferably column chromatography, or by fractional crystallization. The dehydrohalogenation may be performed in a solvent preferably selected from the group consisting of dimethylsolphoxide, dimethylformamide, benzene, hexamethylphosphoric triamide or their mixtures in presence of a base selected for example from the group consisting of 1,5-diazo-bicyclo-[4.3.0]-non-5-ene, or an alkaline hydride, carbonate or alkoxide; 3. Conversion of compounds of formula (XII)

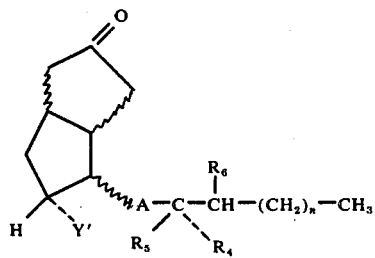

wherein Y', A, R$_6$ and n are as defined above and one of R$_4$ and R$_5$ is a hydrogen atom the other is a hydroxy group, into compounds of formula (XIII)

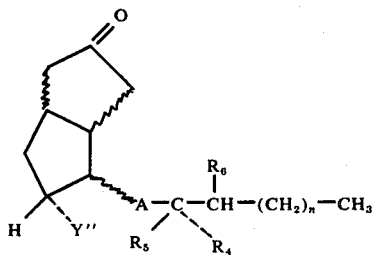

wherein R$_6$ and n are as defined above, Y'' is a known protecting group bound to the cyclopentane ring by an ethereal oxygen atom, and one of R'$_4$ and R'$_5$ is a known protecting group bound to the chain by an ethereal oxygen atom and the other is a hydrogen atom.

The etherification of compounds (XII) to give compounds (XIII) is preceded, when in the compounds of general formula (XII) Y' is an aliphatic, aromatic, or cycloaliphatic acyloxy group, by a saponification, for example by mild treatment with alkalies, to give compounds of formula (XII) wherein Y' is a hydroxy group.

The etherification is preferably carried out with a vinylic ether of formula

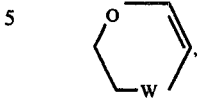

wherein W is —O— or —CH$_2$—, in presence of catalytic amounts of for example phosphorus oxychloride, p-toluenesulphonic acid or benzene sulphonic acid, or with a silyl ether, for instance by reacting a trisubstituted chlorosilane in presence of an acceptor base (for example, a trialkylamine) of the hydrogen halide formed, or with an enol ether, for instance by reaction, in presence of an acid catalyst, with a cyclopentanone or cyclohexanone diacetal, at the reflux temperature in an inert solvent, and distilling the alcohol formed to obtain mixed acetals or enol ethers, according to the quantity of catalyst used or the heating time;

1. reduction of the compound of general formula (XIII) to yield lactol derivatives of general formula (XIV)

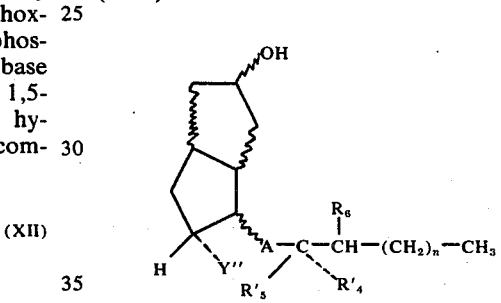

wherein A, Y'', n, R$_6$, R'$_4$ and R'$_5$ are as defined above.

The reduction may be performed by treatment with diisobutylaluminium hydride or sodium bis-(2-methoxyethoxy) aluminium hydride in an inert solvent, for example toluene, n-heptane, n-hexane or benzene or their mixtures, at below −30° C;

5. optional deetherification of the compound of general formula (XIV) to give a compound having the free 11- and 15-hydroxy groups; the deetherification may be accomplished by mild acid hydrolysis, in a solvent miscible with water, with a solution of a mono- or polycarboxylic acid.

In all the compounds mentioned on points (1) to (5), which can be either optically active or racemic compounds, the lactolic ring or, respectively, the lactonic ring, is in the trans-configuration in respect of the side chain. Of the above intermediates, the following are compounds of the invention:

a. the compounds of general formula (XV)

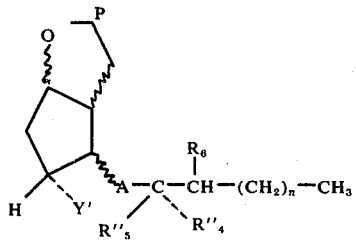

and the racemates thereof, wherein A, $R_6$ and $n$ are as defined above, P is an oxo or hydroxy group, Y' is a hydroxy group or an aliphatic, aromatic, or cycloaliphatic acyloxy group or a known protecting group bound to the ring by an ethereal oxygen atom, and one of $R_4''$ and $R_5''$ is a hydroxy group or a known protecting group bound to the chain by an ethereal oxygen atom and the other is a hydrogen atom or $R_4''$ and $R_5''$ together form an oxo group;

b. the compounds of general formulae (XVI)

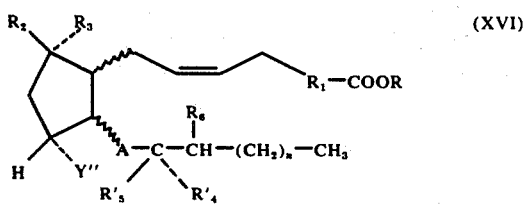
(XVI)

and (XVII)

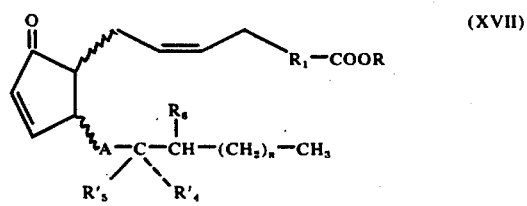
(XVII)

and the racemates thereof,
wherein R is a hydrogen atom, a pharmaceutically acceptable cation or a $C_{1-12}$ alkyl group; $R_1$ is $—CH_2CH_2—$, $—OCH_2—$, $—SCH_2—$, cis$—CH=CH—$, Trans-$CH=CH—$ or $C\equiv C—$; one of $R_2$ and $R_3$ is a hydrogen atom and the other is a hydroxy group or $R_2$ and $R_3$ together form an oxo group; A is

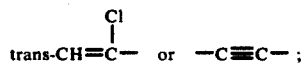

$R_6$ is a hydrogen atom or a $C_{1-4}$ alkyl group; $n$ is 3 or 4; one of $R'_4$ and $R'_5$ is a known protecting group bound to the chain by an ethereal oxygen atom and the other is a hydrogen atom and Y'' is a known protecting group bound to the ring by an ethereal oxygen atom.

In the compounds of general formula (XV) the steric configuration of the lactolic or respectively lactonic, ring, and of the side chain is as already defined above. Analogously in the compounds of general formulae (XVI) and (XVII), the side chains are in the trans-configuration, as defined above.

As stated above, the prostanoic acid derivatives of formulas (I) and (II) can be used in the same applications as the natural prostaglandins.

As hereabove said, prostanoic acid derivatives of formula (I) and (II) can be used in the same applications as natural prostaglandins, in comparison to which they offer however the advantage of a reduced metabolic degradation rate and furthermore of a more selective therapeutic action.

Pharmacological tests have proven, for example, that 5c-9α, 11α, 15-prosten-13-ynoic acid has an excellent spasmogenic activity "in vitro" in the uterus of rat, while tests "in vivo" in guineapigs have shown that 5c-13t-14-chloro-11α, 15S-dihydroxy-9-oxo-prostadienoic acid and 5c-13t-14-chloro-11α, 15R-dihydroxy-9-oxo-prostadienoic acid derivatives own an excellent anti-bronchospastic activity and are therefore useful in the treatment of asthma.

Furthermore, for example, the compounds 5c-9α, 11α, 15R-trihydroxy-prosten-13-ynoic acid, 5c-13t-14-chloro-9α, 11α, 15S-trihydroxy-prostadienoic acid and 5c-13t-14-chloro-9α, 11α15R-trihydroxy-prostadienoic acid possess an excellent anti-ulcer activity, as proved by tests performed "in vivo" in rats, while 5c-11α15S-dihydroxy-9-oxo-prosten-13-ynoic acid has an excellent hypotensive effect in rats.

The compounds of general formula (I) and (II) can be administered orally, parenterally of intravenously, by rectal suppositories or by inhalation. For example, they can be administered by intravenous infusion of a sterile isotonic saline solution at the rate of 0.01 to 10, preferably 0.05 to 1, pg/kg of mammal body weight per minute.

The invention therefore also provides a pharmaceutical composition comprising a compound of general formula (I) and (II) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions.

Examples of substances which can serve as carriers or diluents are water, gelatin, lactose, starches, magnesium stearate, talc, vegetable oil, benzyl alcohol and cholesterol.

The invention is illustrated by the following Examples, wherein the abbreviation "THP", "DIOX", "DMSO" and "DIBA" refer to tetrahydropyranyl, dioxanyl, dimethylsulphoxide and diisobutylaluminium hydride, respectively.

EXAMPLE 1

At room temperature, a solution of 0.02 mol of a 4-ester (acetate, propionate, p-phenylbenzoate) as well as of 4-acetalic ether [tetrahydropyranylether (THP-ether), dioxanylether (DIOX-ether)] of the 5β-hydroxymethyl-2α, 4α-dihydroxy-cyclopentane-1α-acetic acid-γ-lactone, in either the optically active or racemic. form, in 25% dimethylsulfoxide (DMSO) in benzene (100 ml) [for example, a solution of dl-5-α-hydroxymethyl-2α-dihydroxy-cyclopentane-1α-acetic acid-γ-lactone-4-propionate (4.56 g)] is treated with dicyclohexylcarbodiimide (12.5 g) and pyridine trifluoroacetate (19.25 ml) in 25% DMSO in benzene [from pyridine (2 ml) and trifluoroacetic acid (1 ml) in 25 ml of 25% DMSO in benzene].

The mixture is stirred for 4 hours at room temperature and then treated with oxalic acid (5.46 g) in methanol (30 ml) to destroy the excess carbodiimide. After an additional stirring for 45 minutes, the mixture is diluted with water (100 ml) and benzene (150 ml). The precipitate is filtered off and the organic layer is separated, washed with 5% sodium bicarbonate and saturated ammonium sulphate solution to neutrality, dried and evaporated to 20 ml to afford a solution (about 0.02 mol) of a 4-ester (acetate, propionate, p-phenylbenzoate, formiate) or of a 4-acetalic ether (THP-ether, DIOX-ether) of the 5β-formyl-2α,4α-diol-cyclopentane-1α-acetic acid-γ-lactone in either the optically active or the racemic form [for example a solution of about 0.02 mol of the dl-5β-formyl-2α,4α-dihydroxy-cyclopentane-1α-acetic acid-γ-lactone-4-propionate].

EXAMPLE 2

A stirred solution of dry pyridine (3.6 ml) in dry methylene chloride (90 ml), cooled at 5°, is treated with chromic anhydride (3.6 g); the stirring is continued for 15 minutes at 18°–20° C to obtain a deep red solution.

A solution of 0.06 mol of a 4-ester (acetate, propionate, p-phenylbenzoate, formate) or of a 4-acetalic ether (THP-ether, DIOX-ether) of the 5β-hydroxymethyl-2α,4α-dihydroxycyclopentane-1α-acetic acid-γ-lactone, in either the optically active or racemic form [e.g. a solution of 2.11 g of 5β-hydroxymethyl-2α,4α-dihydroxy-cyclopentane-1α-acetic acid-γ-lactone-4-p-phenylbenzoate; m.p. 129.5°–131°, $[\alpha]_D = -87.5°$] in dry methylene chloride is added thereto in a single portion, followed by vigorous stirring for 15 minutes. The organic layer is decanted and the inorganic materials are washed with methylene chloride and combined with the originally obtained organic layer.

After concentration of the solvent to 5–8 ml in vacuo, the residue is diluted with benzene (40–50 ml), treated with decolorant charcoal (1.5 g), filtered to afford, after concentration to 20 ml in vacuo, a benzene solution of about 0.06 mol of a 4-ester (acetate, propionate, p-phenyl-benzoate, formate) or of a 4-acetalic ether (THP-ether, DIOX-ether) of the 5β-formyl(-2α,4α-dihydroxy-cyclopentane-1α-acetic acid-γ-lactone, in either the optically active or the racemic form [e.g. 5β-formyl-2α,4α-dihydroxy-cyclopentane-1α-acetic acid-γ-lactone-4-p-phenylbenzoate].

Alternatively, the benzene solution may be evaporated to dryness in vacuo, and the crude 5β-formyl derivative is then dissolved in dimethoxyethane (20 ml).

EXAMPLE 3

By utilizing one of procedures described in examples 1 and 2, a 4-ester or a 4-acetalic ether of the 5β-hydroxymethyl-2α,4α-dihydroxy-cyclopentane-1α-acetic acid-γ-lactone (dl- or optically active compounds) are oxidized to yield the following 5β-formyl derivatives (dl- or optically active compounds):

5β-formyl-2α,4α-dihydroxy-cyclopentane-1α-acetic acid-γ-lactone-4-formiate;

5β-formyl-2α,4α-dihydroxy-cyclopentane-1α-acetic acid-γ-lactone-4-acetate;

5β-formyl-2α,4α-dihydroxy-cyclopentane-1α-acetic acid-γ-lactone-4 -propionate;

5β-formyl-2α,4α-dihydroxy-cyclopentane-1α-acetic acid-γ-lactone-4-p-phenylbenzoate;

5β-formyl-2α,4α-dihydroxy-cyclopentane-1α-acetic acid-γ-lactone 4-DIOX-ether;

5β-formyl-2α,4α-dihydroxy-cyclopentane -1α-acetic acid-γ-lactone-4-THP-ether.

EXAMPLE 4

A stirred suspension of .80% sodium hydride (NaH) dispersion in mineral oil (0.58g) in dry benzene (70 ml) is slowly treated with dimethyl-(2-oxoheptyl)-phosphonate (4.5 ml) in absolute benzene (15 ml).

When the evolution of hydrogen ceases (1 hour), a solution of 0.02 mol of a 4-ester or of a 4-acetalic ether of the 5β-formyl-2α,4α-dihydroxy-cyclopentane-1α-acetic acid-γ-lactone [e.g. 4-propionate] in benzene, described above (see examples 1, 2 and 3) is added with vigorous stirring to the suspension in benezene of the sodium salt of the phosphonate. After 20 minutes, 10% sodium dihydrogen phosphate solution is added, the organic layer is separated and washed twice with 10% sodium dihydrogen phosphate. Each of the aqueous wash solution is re-extracted with benzene and combined with the orginally obtained layer. The organic phase is washed to neutrality with water, dried and evaporated to dryness to afford a 4-ester formiate, acetate, propionate, p-phenylbenzoate or a 4-acetalic ether (DIOX-ether or THP-ether) of the 5β-(3-oxo-oct-1''-trans-cn-1''-yl)-2α,4α-dihydroxy-cyclopentane-1α-acetic acid-γ-lactone, for example 5.15 g of the corresponding dl-4-propionate derivative.

EXAMPLE 5

A stirred suspension of 80% NaH dispersion in mineral oil (198 mg) in dry dimethoxyethane (30 ml) is slowly treated with dimethyl-(2-oxo-octyl)-phosphonate (1.32 ml) in dry dimethoxyethane to obtain a finely suspension of the sodium salt of the phosphonate (1 hour). A solution of 0.006 mol of a 4-ester of the 5β-formyl-2α,4α-dihydroxy-cyclopentane-1α-acetic acid-γ-lactone [e.g. 4-p- -phenylbenzoate], in dimethoxyethane is then added.

After 1 hour, the reaction mixture is diluted with benzene (2 vol.), the organic layer is washed with a saturated sodium dihydrogen phosphate solution and with a saturated ammonium sulphate solution to neutrality and dried on sodium sulphate.

Removal of the organic solvents in vacuo affords a 4-ester or a 4-acetalic ether of the ''-trans-5β-(1''-non-1-''ene-3''-one)-2α,4α-dihydroxy-cyclopentane-1α-acetic acid-γ-lactone [e.g. 4-p-phenylbenzoate].

Starting from the 4-esters: acetate, propionate, p-phenyl-benzoate of the 5β-formyl-2α,4α-diol-cyclopentane-1α-acetic acid-γ-lactone, using the procedure above described, we prepared the corresponding 4-esters (acetate, propionate, p-phenylbenzoate) of the following 5β-(3''-oxo-non-1''-trans-en-1''-yl)-2α,4α-dihydroxy-cyclopentane-1α-acetic acid-γ-lactone (optically active or racemic).

EXAMPLE 6

By reaction of a 4-ester, acetate, propionate, p-pheny-benzoate of the 5β-formyl-2α,4α-dihydroxy-cyclopentane-1α-acetic acid-γ-lactone in benzene (Example 4) or dimethoxy ethane (Example 5)with the sodium salt of (3-methyl-2-oxoheptyl) dimethoxy phosphonate, we prepared the corresponding ester of the 5β-(4''-methyl-3''-oxo-oct-1''-trans-en-1''-yl)-2α,4α-dihydroxy-cyclopentane-1α-acetic acid-γ-lactone, optically active or racemic.

EXAMPLE 7

Sulphuryl chloride (13.5 ml) is added dropwise with stirring to a solution of dl-5β-(3''-oxo-oct-1''-trans-en-1''-yl)-2α,4α-dihydroxy-cyclopentane-1αacetic acid-γ-lactone-4p-phenyl-benzoate (m.p. 120°–122°; 4.8 g in dry pyridine (95ml), cooled at 0°–5° C, the stirring is continued for a period of 16 hours at 0°–2° C.

The reaction mixture is then poured in cold 2N–H₂SO₄ (500 ml) and extracted several times with ethylacetate (300 ml). The combined organic layers are washed with 4N–H₂SO₄, water, 5% NaHCO₃ and water again to neutrality, dried on sodium sulphate and evaporated to dryness in vacuo.

The crude residue (4.6 g) is then purified by filtration through a short silica gel column (40 g); elution with methylene chloride gives pure dl-5β-(2″-chloro-3-oxo-3″-oct-1″-trans-en-1″-yl)-2α,4α-dihydroxy-cyclopentane-1α-acetic acid-4-p-phenylbenzoate (m.p. 149°–150°; 3.2 g) also named as dl-13t-14-chloro-pentanor-9α,11α-dihydroxy-prost-13-ene-15-oxo-6-oic acid-γ-lactone-11α-p-phenylbenzoate.

EXAMPLE 8

A mixture of isocyanuric chloride (0.9 g), acetic acid (9 ml), 5β-(3″-oxo-non-1″-trans-en-1″-yl)-2α,4α-dihydroxycyclopentane-1α-acetic acid-γ-lactone-4-acetate and acetone (90 ml) is refluxed for 2 hours, concentrated in vacuum to a small volume (25 ml) and then poured into cold 10% sodium carbonate solution. The aqueous phase is extracted repeatedly with ether and the combined organic layers are washed with water, dried on sodium sulphate and evaporated in vacuo to afford a crude chloro derivative, which is adsorbed on a silica gel column.

Elution with methylene chloride affords 5β-(2″-chloro-3″-oxo-non-1″-trans-en-1″-yl)-2α,4α-dihydroxy-cyclopentane-1α-acetic acid-γ-lactone-4-acetate (1.06 g).

EXAMPLE 9

A solution of 5β-(3″-oxo-oct-1″-trans-en-1″-yl)-2α,4α-dihydroxy-cyclopentane-1α-acetic acid-γ-lactone-4-p-phenylbenzoate (m.p. 80°–82° C, [α]$_D$ = −146°; 1.2 g) in acetone (80 ml) is treated with isocyanuric chloride (0.85 g) in the presence of 10% aqueous perchloric acid (8 ml) and refluxed for 2 hours.

The reaction mixture is concentrated in vacuo to small volume, diluted with water and extracted repeatedly with ether.

The combined organic layers are washed with 5% NaHCO$_3$ and water to neutrality, dried (Na$_2$SO$_4$) and evaporated to dryness to afford 5β-(2″-chloro-3″-oxo-oct-1″-trans-en-1″-yl)-2α,4α-dihydroxy-cyclopentane-1α-acetic acid-lactone-4-p-phenylbenzoate (0.85 g), m.p. 150°–151°, [α]$_D$ = −126.5° (CHCl$_3$).

EXAMPLE 10

Sulphuryl chloride (10.5 ml) is added dropwise to a stirred solution of 5α-(3″-oxo-oct-1″-trans-en-1″-yl)-2β,4α-dihydroxy-1β-acetic acid-γ-lactone-4-p-phenylbenzoate (6.52 g) in dry pyridine (80 ml), cooled at 0°–2° and the stirring is continued for 12 hours at this temperature.

The reaction mixture is then poured into ice-water, acidified and repeatedly extracted with ethyl acetate. The combined organic layers are washed to neutrality, dried (Na$_2$SO$_4$) and evaporated to dryness to afford, after crystallization from methanol-ether, the 5α-(2″-chloro-3″-oxo-oct-1″-trans-en-1″-yl)-2β,4α-dihydroxy-cyclopentane-1β-acetic acid-γ-lactone-4-p-phenylbenzoate (5.8 g) also named as 13t-14-chloro-pentanor-9β,11α-dihydroxy-8,12-diiso-prost-13-ene-15-one-6-oic-acid-γ-lactone-11-p-phenylbenzoate.

EXAMPLE 11

Using the 5α-(4″-methyl-3″-oxo-oct-trans-1″-en-1″-yl)-2β,4α-dihydroxy cyclopentyl-1β-acetic acid-γ-lactone-4-p-phenylbenzoate (1.2 g) in the procedure of Example 9 the following is prepared:

5α-(2″-chloro-4″-methyl-3″-oxo-oct-trans-1″-en-1″-yl)-2β,4α-dihydroxycyclopentyl-1β-acetic acid-γ-lactone-4-p-phenylbenzoate (0.93 g), also named as 13t-14-chloro-16-methyl-pentanor-9β,11α-dihydroxy-8,12-diiso-prost-13-ene-15-one-6-oic acid-γ-lactone-11-p-phenylbenzoate.

EXAMPLE 12

A stirred solution of 5α-(3″-oxo-non-trans-1″-en-1″-yl)-2β,4α-dihydroxycyclopentyl-1β-acetic acid-γ-lactone-4-p-phenylbenzoate (0.97 g) in dry pyridine (15 ml), cooled at 0° C, is treated with sulphuryl chloride (1.6 ml) and allowed at 0° for 12 hours under stirring.

The reaction mixture is then poured into ice-water, acidified with 4N—H$_2$SO$_4$ and extracted with ethylacetate. The organic extracts are washed to neutrality, dried (Na$_2$SO$_4$) and evaporated to dryness to afford, after crystallization from methanol, the 5α-(2″-chloro-3″-oxo-non-trans-1″-en-1″-yl)-2β,4α-dihydroxycyclopentyl-1β-acetic acid-γ-lactone-4-p-phenylbenzoate (0.64 g), also named as 13t-14-chloro-9β,11α-diol-20ω-homopentanor-8,12-diiso-prost-13-ene-15-one-6-oic acid-γ-lactone-11-p-phenylbenzoate.

EXAMPLE 13

To a stirred solution of dl-5β-(4″-methyl-3″-oxo-oct-1″-en-1″-yl)-2α,4α-dihydroxycyclopentyl-1α-acetic acid-γ-lactone-4-formiate (2.3 g) in dry pyridine, sulphuryl chloride (2.5 mol equiv.) is added dropwise; the reaction mixture is allowed to stand at 0° for 10 hours under stirring. It is then diluted with ice-water, acidified to pH 3 with 4N H$_2$SO$_4$ and extracted with ether-methylene chloride (4:1). The combined organic extracts are washed to neutrality, dried (Na$_2$SO$_4$) and evaporated to dryness in vacuo to afford, after crystallization the dl-5β-(2″-chloro-4″-methyl-3″-oxo-oct-1″-en-1″-yl)-2α,4α-dihydroxycyclopentyl-1α-acetic acid γ-lactone-4-formiate (2.05 g) also named as dl-13-14-chloro-16-methyl-9α,11α-dihydroxy-pentanor-prost-13-ene-15-one-6-oic acid-γ-lactone-11-formiate.

EXAMPLE 14

Using the trans-enone-lactones prepared in Example 4, 5 and 6, in the procedure of Examples 7 and 13 the 11-esters (acetate, p-phenylbenzoate, formiate, propionate) and 11-acetalic ethers (11-THP-ether), (11-DIOX-ether) of the following compounds:

13t-14-chloro-9α,11α-dihydroxy-pentanor-prost-13-ene-15-one-6-oic acid-γ-lactone;
13t-14-chloro-9α,11α-dihydroxy-20ω-homo-pentanor-prost-13-ene-15-one-6-oic acid-γ-lactone;
13t-14-chloro-16-methyl-9α,11α-dihydroxy-pentanor-prost-13-ene-15-one-6-oic acid-γ-lactone, are prepared.

EXAMPLE 15 dl-14-chloro-13t-9α,11α-dihydroxy-pentanor-prost-13-ene-15-one-6-oic acid-γ-lactone-11-p-phenylbenzoate (2.55 g) in dry dimethoxyethane (39.5 ml) is added to a 0.065M-zinc borohydride in ether (220 ml) under vigorous stirring. The stirring is continued for 2½ hours; the excess reagent is then destroyed by cautious addition of 2N—H$_2$SO$_4$ and the organic layer is separated and washed with 2N—H$_2$SO$_4$ and water to neutrality. Each of the aqueous wash solutions is re-extracted with ether and combined with the organic phase. After drying (Na$_2$SO$_4$) and removal of the solvents in vacuo, the residue, consisting of a mixture of the two epimeric alcohols 15S and 15R, is absorbed on a silica (0.45 kg) column. Elution with ethyl ether give the dl-13t-14-chloro-9α,11α,15S-trihydroxy-pentanor-prost-13-ene-6-oic acid-γ-lactone-11-p-phenylbenzoate (1.6 g) as an oil and the dl-13t-14-chloro-9α,11α,15R-trihydroxy-pentanor-prost-13-ene-6-oic acid-γ-lactone-11-p-phenylbenzoate (0.9 g; m.p. 126°–128° C).

EXAMPLE 16

To a stirred 0.05M-zinc borohydride in ether (500 ml), a solution of 13t-14-chloro-9α,11α-dihydroxy-pentanor-prost-13-ene-15-one-6-oic acid-γ-lactone-11-p-phenylbenzoate (4.8 g) in dry dimethoxyethane is added. After 15 minutes, the excess reagent is destroyed by cautious addition of saturated sodium chloride solution.

The zinc hydroxyde precipitate is dissolved by adding $2N-H_2SO_4$, and the organic layer is separated and washed with 2N sulphuric acid and water to neutrality. Each of the aqueous wash solutions is re-extracted with ether and combined with the organic phase.

After drying ($Na_2SO_4$) and removal of the solvents in vacuo, the residue is absorbed on silica (0.9 kg) column. By elution with ether, 13t-14-chloro-9α,11α,15S-trihydroxypentanor-prost-13-ene-6-oic acid-γ-lactone-11-p-phenylbenzoate [2.7 g; $[\alpha]_D = -79.5°$ ($CHCl_3$)] and 13t-14-chloro-9α,11α,15R-trihydroxy-pentanor-prost-13-ene-6-oic acid-γ-lactone-11-p-phenylbenzoate [2.2 g; m.p. 83°–85° C; $[\alpha]_D = -89°$], are obtained.

EXAMPLE 17

Using the chloro-trans-enone-lactones prepared in Example 14, in the procedure of Examples 15, 16, the 11-esters (acetate, formiate, propionate, p-phenylbenzoate) and the 11-acetalic ethers (11-THP-ether, 11-DIOX-ether) of the following compounds:

13t-14-chloro-9α,11α,15S-trihydroxy-pentanor-prost-13-ene-6-oic acid-γ-lactone;

13t-14-chloro-9α,11α,15S-trihydroxy-pentanor-20ω-homo-prost-13-ene-6-oic acid-γ-lactone;

13t-14-chloro-16-methyl-9α,11α,15S-trihydroxy-pentanor-prost-13-ene-6-oic acid-γ-lactone;

13t-14-chloro-9α,11α,15R-trihydroxy-pentanor-prost-13-ene-6-oic acid-γ-lactone;

13t-14-chloro-9α,11α,15R-trihydroxy-pentanor-20ω-homo-prost-13-ene-6-oic acidγ-lactone;

13t-14-chloro-16-methyl-9α,11α,15R-trihydroxy-pentanor-prost-13-ene-6-oic acid-γ-lactone are obtained.

EXAMPLE 18

Sodium borohydride (40 mg) is added to a stirred solution of 13t-14-chloro-9α,11α-dihydroxy-pentanor-8,12-diiso-prost-13-ene-15-one-6-oic acid-γ-lactone-4-p-phenylbenzoate (0.4 g) in methanol (10 ml) and methylene chloride (5 ml), cooled to 0°–5° C. The stirring is continued for 30 minutes, the excess reagent is destroyed by addition of saturated $NaH_2PO_4$ solution (1.5 ml) and the mixture is evaporated almost to dryness in vacuo. After dilution with ethyl acetate, the organic layer is washed with water to neutrality, dried ($Na_2SO_4$) and evaporated to dryness to afford a crude product which is absorbed on silica (80 g) column.

Elution with isopropyl ether-ethyl ether (75:25) gives 13t-14-chloro-9β,11α,15R-trihydroxy-pentanor-8,12-diiso-prost-13-ene-6-oic acid-γ-lactone-11-p-phenylbenzoate (0.15 g) and 13t-14-chloro-9β,11α,15S-trihydroxypentanor-8,12-diiso-prost-13-ene-6-oic acid-γ-lactone-11-p-phenylbenzoate, also named as 5α-(2″-chloro-oct-trans-1″-en-1″-yl)-2β,4α,3″S-trihydroxycyclopentyl-1β-acetic acid-γ-lactone-4-p-phenylbenzoate.

EXAMPLE 19

Using the chloro-trans-enone-lactones prepared in Examples 11 and 12, in the procedure of Examples 15,16 (reduction with zinc borohydride in dimethoxyethane-ether) and 18 (reduction with sodium borohydride in methanol-methylene chloride) we prepared:

13t-14-chloro-9β,11α,15S-trihydroxy-pentanor-20ω-homo-8,12-diiso-prost-13-ene-6-oic acid-γ-lactone-11-p-phenylbenzoate;

13t-14-chloro-9β,11α,15S-trihydroxy-pentanor-16-methyl-8,12-diiso-prost-13-ene-6-oic acid-γ-lactone-11-p-phenylbenzoate;

13t-14-chloro-9β,11α,15R-trihydroxy-pentanor-20ω-homo-8,12-diiso-prost-13-ene-6-oic acid-γ-lactone-11-p-phenylbenzoate;

13t-14-chloro-9β,11α,15R-trihydroxy-pentanor-16-methyl-8,12-diiso-prost-13-ene-6-oic acid-γ-lactone-11-p-phenylbenzoate.

EXAMPLE 20

A solution of 13t-14-chloro-9α,11α,15S-trihydroxy-pentanor-prost-13-ene-6-oic acid-γ-lactone-11-p-phenylbenzoate (1.6 g) in methanol is treated with 7.8 ml of 20% aqueous potassium carbonate, refluxed for 1 hour, cooled at room temperature and treated with $4N-H_2SO_4$ (6 ml). The mixture is stirred for 3 hours at room temperature, the precipitate salts are filtered and the filtrate is concentrated in vacuo to remove the methanol. The residue is dilute with ethylacetate and the organic phase is separated. The aqueous layer is repeatedly extracted with ethyl acetate (5 × 25 ml) and then the organic layers are combined, washed first with saturated sodium bicarbonate to remove the p-phenylbenzoic acid and then with saturated sodium chloride solution till neutral, dried ($Na_2SO_4$) and evaporated to dryness in vacuo to afford the 13t-14-chloro-9α,1-1α,15S-trihydroxy-pentanor-prost-13-ene-6-oic acid-γ-lactone, also named as 5β-(3″-chloro-oct-trans-1″-en-1″-yl)-2α,4α,3″S-trihydroxy-cyclopentyl-1α-acetic acid-γ-lactone, as an oil: $[\alpha]_D = -17.8°$ ($CHCl_3$); 0.93 g (yield 92%).

This compound, in benzene (30 ml) is refluxed with the acqueous azeotrope being removed by a water trap, the cooled solution is treated with 2,3-dihydropyran (1.2 ml) and p-toluenesulphonic acid (10 mg) in benzene (3 ml).

After 6 hours at room temperature, the benzene layer is washed with 5% sodium bicarbonate and water till neutral, and the solvent is evaporated in vacuo to afford a crude product which is absorbed on a silica (30 g) column. Elution with cyclohexane/ethylacetate (80:20) affords, as an oil, pure 13t-14-chloro-9α,1-1α,15S-trihydroxy-pentanor-prost-13-ene-6-oic acid-γ-lactone-9α,15S-bis-THP-ether (1.41 g); $[\alpha]_D = -58.6°$ ($CHCl_3$), also named as 5β-(2″-chloro-oct-trans-1″-en-1″-yl)-2α,4α,3″S-trihydroxy-cyclopentyl-1α-acetic acid-γ-lactone-4α,3″S-bis THP-ether.

EXAMPLE 21

13t-14-chloro-9β,11α,15S-trihydroxy-pentanor-8,12-diiso-prost-13-ene-6-oic acid-γ-lactone-11-p-phenylbenzoate (2.4 g) in dry methanol (30 ml) is treated with anhydrous potassium carbonate (0.77 g) under stirring for 40 minutes at 10° C. The reaction mixture is neutralized with 15% aqueous acetic acid, evaporated almost to dryness and diluted with ether.

The organic layer is repeatedly washed with 5% NaHCO$_3$ and with water till neutral, dried (Na$_2$SO$_4$) and the solvent is evaporated in vacuo to afford 13t-14-chloro-9β,11α,15S-trihydroxy-pentanor-8,12-diiso-prost-13-ene-6-oic acid-γ-lactone (1.45 g).

This compound, in dry benzene (30 ml) is treated with 1,4-diox-2-ene (2.2 ml) and p-toluenesulphonic acid (9.5 mg) in benzene (4 ml).

After 6 hours at room temperature, the organic phase is washed with 5% NaHCO$_3$ and with water till neutral and the solvents are evaporated to dryness in vacuo to afford a crude product which is absorbed on silica (60 g) column. Elution with cyclohexane-ethylacetate (80:20) affords pure 13t-14-chloro-9β,11α,15S-trihydroxy-pentanor-8,12-diiso-prost-13-ene-6-oic acid-γ-lactone-11α,15S-bis-DIOX-ether (2.12 g) also named as 5α-(2''-chloro-oct-trans-1''-ene-1''-yl)-2β,4α,3''S-trihydroxy-cyclopentyl-1β-acetic acid-γ-lactone-4α,3''S-bis-dioxa-1'',4''-nylether.

EXAMPLE 22

Starting from an 11-ester (acetate, propionate, formiate, p-phenylbenzoate) of a 13t-14-chloro-9,11,15-trihydroxy-pentanor-prost-13-ene-6-oic acid-γ-lactone and following the procedures described in the Examples 20 and 21, we prepare the free hydroxy derivatives, the 11α,15-bis-THP-ether and the 11α,15-bis-DIOX-ether of the following compounds:

13t-14-chloro-9α,11α,15S-trihydroxy-pentanor-prost-13-ene-6-oic acid-γ-lactone;
13t-14-chloro-9α,11α,15S-trihydroxy-pentanor-20ω-homo-prost-13-ene-6-oic acid-γ-lactone;
13t-14-chloro-16-methyl-9α,11α,15S-trihydroxy-pentanor-prost-13-ene-6-oic acid-γ-lactone;
13t-14-chloro-9α,11α,15R-trihydroxy-pentanor-prost-13-ene-6-oic acid-γ-lactone;
13t-14-chloro-9α,11α,15R-trihydroxy-pentanor-20ω-homo-prost-13-ene-6-oic acid-γ-lactone;
13t-14-chloro-16-methyl-9α,11α,15R-trihydroxy-pentanor-prost-13-ene-6-oic acid-γ-lactone;
13t-14-chloro-9β,11α,15S-trihydroxy-pentanor-8,12-diiso-prost-13-ene-6-oic acid-γ-lactone;
13t-14-chloro-9β,11α,15S-trihydroxy-pentanor-20ω-homo-8,12-diiso-prost-13-ene-oic acid-γ-lactone;
13t-14-chloro-16-methyl-9β,11α,15S-trihydroxy-pentanor-8,12-diiso-prost-13-ene-6-oic acid-γ-lactone;
13t-14-chloro-9β,11α,15R-trihydroxy-pentanor-8,12-diiso-prost-13-ene-6-oic acid-γ-lactone;
13t-13-chloro-9β,11α,15R-trihydroxy-pentanor-20ω-homo-8,12-diiso-prost-13-ene-6-oic acid-γ-lactone;
13t-14-chloro-16-methyl-9β,11α,15R-trihydroxy-pentanor-8,12-diiso-prost-13-ene-6-oic acid-γ-lactone.

EXAMPLE 23

Lithium borohydride (200 mg) is added, portion wise, to a stirred solution of an 11α-acetalic ether (11α-THP ether, 11α-DIOX-ether), of the 13t-14-chloro-9α,11α-dihydroxypentanor-prost-13-ene-15-one-6-oic acid -γ-lactone (2.2 g) in methanol (40 ml); the stirring is continued for 30 minutes. The excess reagent is then destroyed by addition of a saturated sodium dihydrogen phosphate solution and the reaction mixture is concentrated to small volume in vacuo, diluted with ether and washed with water to neutrality. After drying (Na$_2$SO$_4$) and removal of solvents in vacuo, the residue is absorbed on a silica (400 g) columm and eluted with isopropyl ether: ethylether (50:50) to afford 1.05 and 0.95 g, respectively of the two opimers 15S and 15R of the 13t-14-chloro-9α,11α,15-trihydroxy-pentanor-prost-13-ene-6-oic acid -γ-lactone-11α-monoacetalic ether (11α-THP-ether, 11α,-DIOX-ether), which are optionally reacted with 2,3-dihydropyran and 1,4-diox-2ene to give the corresponding 11α,15-bis-THP-ether and 1α,15-bis-DIOX-ether.

EXAMPLE 24

Under a nitrogen atmosphere, a stirred solution of 13t-14-chloro-9α,11α,15S-triol-pentanor-prost-13-ene-6-oic acid-γ-lactone-11α,15S-bis-THP-ether (1.41 g) in dry toluene (43 ml), cooled at −60°, is treated over 20 minutes with 0.5 N diisobutyl aluminumhydride solution (15.8 ml). The mixture is stirred for an additional 30 minutes at −60° and then treated with 12 ml of a 2M-isopropaol solution in toluene. After 10 minutes the mixture is warmed up to 0°–2°, treated with water, sodium sulphate (2.8 g) and celite (1.2 g) and is then filtered. The filtrate is evaporated to dryness in vacuo to afford, as an oil, 13t-14-chloro-9α,11α,15S-triol-pentanor-prost-13-ene-6-ale-γ-lactol-11α,15S-bis-THP-ether (1.38 g), [α]$_D$=62° (CHCl$_3$), also named as 5β-(2''-chloro-oct-1''-trans-en-1''-yl)-2α,4α,3''S-trihydroxy-cyclopentyl-1α-ethanol-γ-lactol-4α,3''bis-THP-ether.

Under a nitrogen atmosphere, freshly sublimed potassium tert-butoxide (1.4 g) in dry (by distillation from calcium hydride, H$_2$O ≤ 0.02%) DMSO (20 ml) is added to a stirred solution of this lactol (1.18 g) and of triphenyl (4-carboxybutyl) phosphonium bromide (2.8 g) in dry DMSO (20 ml) and is cooled in a ice-water bath so that the temperature of the reaction mixture does not exceed 20° C.

The deep red solution is stirred for additional 30 minutes at room temperature, diluted with ice-water (70 ml).

The aqueous phase is extracted repeatedly with ether until all the triphenyl phosphoxide has been removed, and the combined organic layers are re-extracted with 5% sodium bicarbonate. The pH of the combined aqueous phases is adjusted to 4.5–4.7 with 4N-sulphuric acid, followed by extraction with ether pentane (1:1). The organic layers are combined, washed with saturated ammonium sulphate solution, dried (Na$_2$SO$_4$) and evaporated in vacuo to afford the 5c-13t-14-chloro-9α,11α,15S-trihydroxy-prosta-5,13-diene-1-oic acid-11α,15S-bis-THP-ether (1.41 g), [α]$_D$ = −41.7° (CHCl$_3$), also named as 14-chloro-PGF$_{2α}$ -11α,15S-bis-THP-ether.

EXAMPLE 25

Under a nitrogen atmosphere a mixture of 70% solution of sodium bis-(2-methoxyethoxy)aluminium hydride in benzene (2.24 ml) and toluene (8 ml) is added dropwise to a stirred solution of 13t-14-chloro-9α,1-1α,15R-trihydroxy-prost-13-ene-6-oic acid-γ-lactone-11α,15S-bis-THP-ether (2.6 g), [α]$_D$ = +56° (CHCl$_3$)

in dry toluene (60 ml), cooled at −50° to −55° C. The stirring is continued for 3 hours, the excess reagent is then destroyed by cautious addition of 5% acetone solution in toluene.

After 10 minutes the mixture is warmed up to 0°–2° C, treated with a saturated sodium dihydrogen phosphonate solution (3 ml) and the crystalline inorganic precipitate is filtered.

The filtrate is evaporated to dryness in vacuo to give 13t-14-chloro-9α,11α,15R-trihydroxy-pentenor-prost-13-ene-6-ale-γ-lactol-11α,15S-bis-THP-ether (2.55 g) $[\alpha]_D = +32.4°$ (CHCl$_3$), as an oil.

EXAMPLE 26

Using the lactone 11,15-bis-acetalic ethers prepared in Example 22, in the procedure of Examples 24 (diisobutyl aluminium hydride reduction) and 25 (sodium bis-(2-methoxyethoxy) aluminium hydride reduction), we prepare the 11,15 bis-acetalic ethers (bis-THP-ether, bis-DIOX-ether) of the following lactol compounds:

13t-14-chloro-9α,11α,15S-trihydroxy-pentanor-prost-13-ene-6-ale-γ-lactol;
13t-14-chloro-9α,11α,15S-trihydroxy-pentanor-20ω-homo-prost-13-ene-6-ale-γ-lactol;
13t-14-chloro-16-methyl-9α,11α,15S-trihydroxy-pentanor-prost-13-ene-6-ale-γ-lactol;
13t-14-chloro-9α,11α,15R-trihydroxy-pentanor-prost-13-ene-6-ale-γ-lactol;
13t-14-chloro-9α,11α,15R-trihydroxy-pentanor-20ω-homo-prost-13-one-6-ale-γ-lactol;
13t-14-chloro-16-methyl-9α,11α,15R-trihydroxy-pentanor-prost-13-ene-6-ale-γ-lactol;
13t-14-chloro-9β,11α,15R-trihydroxy-pentanor-8,12diiso-prost13-ene-6-ale-γ-lactol;
13t-14-chloro-9β,11α,15R-trihydroxy-pentanor-20ω-homo-8,12-diiso-prost-13-ene-6-ale-γ-lactol;
13t-14-chloro-16-methyl-9β,11α,15R-trihydroxy-pentanor-8,12-diiso-prost-13-ene-6-ale-γ-lactol;
13t-14-chloro-9β,11α,15S-trihydroxy-pentanor-8,12-diiso-prost-12-ene-6-ale-γ-lactol;
13t-14-chloro-9β,11α,15S-trihydroxy-pentanor-20ω-homo-8,12-diiso-prost-13-ene-6-ale-ω-lactol;
13t-14-chloro-16-methyl-9β,11α,15S-trihydroxy-pentanor-8,12-diiso-prost-13-ene-6-ale-γ-lactol.

EXAMPLE 27

7.2% diisobutyl aluminium hydride solution in toluene (16 ml) is added over 15 minutes to a stirred solution of 13t-14-chloro-9α,11α,15S-trihydroxy-pentanor-prost-13-ene-6-oic acid-γ-lactone-11-p-phenylbenzoate (1.15 g) in dry toluene, cooled at −60° and the stirring is continued for 30 minutes. The reaction mixture is taken treated with 2N-isopropanol solution in toluene and after 10 minutes is warmed up to 0°–2°, treated with water (1 ml), anhydrous sodium sulphate (2 g) and celite (2.5 g) and filtered.

The filtrate is evaporated to dryness in vacuo to afford a crude product which is absorbed on silica (30 g) column. Elution with cyclohexane-ethylacetate 4:6 gives the 13t:14-chloro-9α,11α,15S-trihydroxy-pentanor-prost-13-ene-6-ale-γ-lactol.

Starting from an 11-ester of a 13t-14-chloro-9α,11α,15-trihydroxy-pentanor-prost-13-ene-6-oic acid-γ-lactone, in similar way by reduction with diisobutylaluminium hydride we prepared the following compounds:

13t-14-chloro-9α,11α,15R-trihydroxy-pentanor-prost-13-ene-6-ale-γ-lactol;
13t-14-chloro-16-methyl-9α,11α,15S-trihydroxy-pentanor-prost:-13-one-6-ale-γ-lactol;
13t-14-chloro-16-methyl-9α,11α,15R-trihydroxy-pentanor-prost-13-ene-6-ale-γ-lactol;
13t-14-chloro-9α,11α,15S-trihydroxy-pentanor-20ω-homo-prost-13-ene-6-ale-γ-lactol;
13t-14-chloro-9α,11α,15R-trihydroxy-pentanor-20ω-homo-prost-13-ene-6-ale-γ-lactol;
13t-14-chloro-9β,11α,15R-trihydroxy-pentanor-8,12-diiso-prost-13-ene-6-all-γ-lactol;
13t-14-chloro-9β,11α,15S-trihydroxy-pentanor-8,12-diiso-prost-13-ene-6-ale-γ-lactol;
13t-14-chloro-16-methyl-9β,11α,15S-trihydroxy-pentanor-8,12-diiso-prost-13-ene-6-ale-γ-lactol;
13t-14-chloro-16-methyl-9β,11α,15R-trihydroxy-pentanor-8,12-diiso-prost-13-ene-6-ale-γ-lactol;
13t-14-chloro-9β,11α,15S-trihydroxy-pentanor-20ω-homo-8,12-diiso-prost-13-ene-6-ale-γ-lactol;
13t-14-chloro-9β,11α,15R-trihydroxy-pentanor-20ω-homo-8,12-diiso-prost-13-ene-6-ale-γ-lactol.

EXAMPLE 28

Freshly sublimed potassium tert-butoxide (1.3 equiv., 0.27 g) is added to a stirred solution of dl-13t-14-chloro-9α,11α,15R-trihyroxy-pentanor-prost-13-ene-6-oic acid-γ-lactone-11,15-bis-THP-ether (0.85 g) in DMSO (5 ml). After 6 hours at room temperature, the reaction mixture is diluted with water, acidified to pH 4 and extracted with ether.

The organic layer is washed with water until neutral, dried (Na$_2$SO$_4$) and after removal of solvent in vacuo the residue is absorbed on silica gel column. Elution with cyclohexane-ether (1:1) affords pure dl-9α,11α,15R-trihydroxy-pentanor-prost-13-yn-6-oic acid-γ-lactone-11,15-bis-THP-ether (0.62 g).

Starting with the chloro-lactone-11,15-bis-acetalic ethers prepared in Example 22, and following the same procedure, we prepared the 11,15-bis-acetalic ethers (bis-THP-ether, bis-DIOX-ether) of the following compound as dl- and as optically active compound:

9α,11α,15S-trihydroxy-pentanor-prost-13-yn-6-oic acid-γ-lactone; 1
16-methyl-9α,11α,15S-trihydroxy-pentanor-prost-13-yn-6-oic acid-γ-lactone;
9α,11α,15R-trihydroxy-pentanor-prost-13-yn-6-oic acid-γ-lactone;
9α,11α,15-trihyroxy-pentanor-20ω-homo-prost-13-yn-6-oic acid-γ-lactone;
16-methyl-9α,11α,15R-trihydroxy-pentanor-prost-13-yn-6-oic acid-γ-lactone;
9β,11α,15R-trihydroxy-pentanor-8,12-diiso-prost-13yn-6-oic acid-γ-lactone;
9β,11α,15-trihyroxy-pentanor-20ω-homo-8,12-diiso-prost-13-yn-6-oic acid-γ-lactone;
16-methyl-9β,11α,15R-trihydroxy-pentanor-8,12-diiso-prost-13-yn-6-oic acid-γ-lactone;
9β,11α,15S-trihyroxy-pentanor-8,12-diiso-prost-13-yn-6-oic acid-ω-lactone;
9β,11α,15S-trihydroxy-pentanor-20ω-homo-8,12-diiso-prost-13-yn-6-oic acid-γ-lactone;
16-methyl-9β,11α,15S-trihydroxy-pentanor-8,12-diiso-prost-13-yn-6-oic acid-γ-lactone.

EXAMPLE 29

A mixture of 13t-14-chloro-9α,11α,15S-trihydroxy-pentanor-prost-13-en-6-oic acid-γ-lactone-11α,15S-bis-DIOX-ether (3.2 g) and 1.5-diazabicyclo-[4.3.0]-non-5-ene (1.3 equiv.) in benzene is heated at 50° for 6 hours and filtered. After concentration to small volume the reaction mixture is absorbed on a neutral aluminium oxide (15 g) column and eluted with benzene to afford 9α,11α,15S-trihydroxy-pentanor-prest-13-yn-6-oic acid-γ-lactone-11α,15S-bis-DIOX-ether (1.6 g).

EXAMPLE 30

The 13t-14-chloro-9α,11α,15R-trihydroxy-pentanor-prost-13-ene-6-oic acid-γ-lactone-11α-p-phenylbenzoate (2.1 g) is converted by reaction with 2,3-dihydropiran in benzene in the presence of p-toluensulphonic acid into the 15R-THP-ether (2.48 g). This compound is reacted with 1.3 equiv. (0.6 g) of 1.5-diazobicyclo-[4.3.0]-non-5-ene in benzene for 16 hours at room temperature. The reaction mixture is then filtered, concentrated to small volume to afford after filtration of neutral aluminium oxide 9α,11α,15R-trihydroxy-pentanor-prost-13-yn-6-oic acid-γ-lactone-11α-p-phenylbenzoate-15R-THP-ether (2.38 g).

A solution of this product in acetone is treated with 0.5N-oxalic acid solution (50 ml) at reflux temperature for 30 minutes, to afford other concentration, dilution with water and filtration, the 9α,11α,15R-trihydroxy-pentanor-prost-13-yn-6-oic acid-γ-lactone-11α-p-phenyl-benzoate (1.72 g).

A solution of this product in acetone (30 ml) is treated with Jones reagent (3.5 ml) at −10° C for 5 minutes, the reaction mixture is diluted with benzene (150 ml) and the organic layer is washed till neutral with a saturated ammonium sulphate solution. Evaporation of solvents gives 9α,11α-dihydroxy-pentanor-prost-13-yn-15-one-6-oic acid -γ-lactone (1.25 g).

To a stirred solution of 0.065M zinc borohydride in ether (220 ml), a solution of this compound (2.6 g) in dry dimethoxyethane is added. After 2½ hours the excess reagent is destroyed by treatment with 2N—$H_2SO_4$, the organic layer is separated, washed till neutral with saturated $(NH_4)_2SO_4$ solution, dried $(Na_2SO_4)$ and evaporated to dryness to give a mixture of two 15S and 15R-epimeric alcohols, which is absorbed on silica (130 g) column.

Following elution with isopropyl ether affords 9α,11α,15S-trihydroxy-pentanor-prost-13-yn-6-oic acid-γ-lactone-11α-p-phenylbenzoate (1.02 g) and its 15R-epimer (0.82 g).

The 15S-epimer (1.43 g) is then treated in methanol (25 ml) with 20% aqueous potassium carbonate solution (6 ml) at reflux temperature for 1 hour. The reaction mixture is cooled, acidified and stored for 2 hours at room temperature.

The precipitate salts are filtered, the filtrate is concentrated in vacuo to small volume to afford after extraction with ether-methylene chloride (4:1) 9α,11α,15S-trihydroxy-pentanor-prost-13-yn-6-oic acid-γ-lactone (0.81 g). Following reaction in benzene of this product with 2,3-dihydropiran in the presence of catalytical amounts of p-toluensulphonic acid affords the 9α,11α,15S-trihydroxy-pentanor-prost-13-yn-6-oic acid-γ-lactone-11α,15S-bis-THP-ether (1.32 g).

EXAMPLE 31

A solution of 9α,11α,15S-trihydroxy-pentanor-prost-13-yn-6-oic acid-γ-lactone-11α,15S-bis-THP-ether (1.32 g) in toluene is reacted with a 0.5M solution of diisobutyl aluminium hydride in toluene (10 ml) at −60° for 30 minutes. The excess reagent is destroyed by addition of a 2M solution of isopropanol in toluene (6 ml). After 15 minutes, the reaction mixture is warmed to 0°, treated with water (1.2 g), sodium sulphate (2.8 g), celite (2.8 g) and filtered.

The filtrate is evaporated to dryness in vacuo to give 9α,11α,15S-trihydroxy-pentanor-prost-13-yn-6-ale-γ-lactol-11α,15S-bis-THP-ether (1.25 g).

EXAMPLE 32

Using the 9,11,15-trihydroxy-pentanor-prost-13-yn-6-oic acid-γ-lactone-11α,15-bis-acetalic ethers prepared in the Example 28 in the procedure of the Examples 24, 31 (reduction with diisobutylaluminium hydride) and 25 (reduction with sodium-bis-(2-methoxyethoxy) aluminium hydride, we prepare the 11α,15-bis-acetalic ethers (11α,15-bis-THP-ether, 11α,15-bis-DIOX-ether) of the following lactol derivatives:

9α,11α,15S-trihydroxy-pentanor-prost-13-yn-6-ale-γ-lactol;

9α,11α,15S-trihydroxy-pentanor-20ω-homo-prost-13-yn-6-ale-γ-lactol;

16-methyl-9α,11α,15S-trihydroxy-pentanor-prost-13-yn-6ale-γ-lactol;

9α,11α,15R-trihydroxy-pentanor-prost-13-yn-6ale-γ-lactol;

9α,11α,15R-trihydroxy-pentanor-20ω-homo-prost-13-yn-6-ale-γ-lactol;

16-methyl-9α,11α,15R-trihydroxy-pentanor-prost-13-yn-6-ale-γ-lactol;

9β,11α,15R-trihydroxy-pentanor-8,12-diiso-prost-13-yn-6-ale-γ-lactol;

9β,11α,15S-trihydroxy-pentanor-8,12-diiso-prost-13-yn-6-ale-γ-lactol;

9β,11α,15R-trihydroxy-pentanor-20ω-homo-8,12-diiso-prost-13-yn-6-ale-γ-lactol;

9β,11α,15S-trihydroxy-pentanor-20ω-homo-8,12-diiso-prost-13-yn-6-ale-γ-lactol;

16-methyl-9β,11α,15R-trihydroxy-pentanor-8,12-diiso-prost-13-yn-6-ale-γ-lactol;

16-methyl-9β,11α,15S-trihydroxy-pentanor-8,12-diiso-prost-13-yn-6-ale-γ-lactol.

EXAMPLE 33

Under a nitrogen atmosphere, a suspension of 80% sodium hydride (0.78 g) in dry dimethylsulphoxide (23 ml) is heated with stirring at 60° until the evolution of hydrogen ceases (3 hours).

The stirred mixture of methyl sulphinyl carbanide cooled to 5°–10° is treated with triphenyl (4-carboxy butyl) phosphonium bromide (5.78 g) in dry DMSO (23 ml); the deep orange-red solution of the ylide is then treated with a solution of 13t-14-chloro-9α,11α,15S-trihydroxypentanor-prost-13-ene-6-ale-γ-lactol-11,15-bis-THP-ether (1.35 g) in dry DMSO (10 ml). The mixture is stirred for additional 45 minutes and then diluted with ice-water (50 ml) and extracted repeatedly with ether until all the triphenylphosphoxide has been removed and the combined organic layers are re-extracted with 5% sodium bicarbonate. The pH of the combined aqueous phases is adjusted to 4.5–4.7 with 4N-sulphuric acid, followed by extraction with ether-pentane (1:1).

The organic layers are combined, washed with saturated $(NH_4)_2SO_4$ solution, dried $(Na_2SO_4)$ and evaporated to dryness to afford a mixture (80:20) of 5c,13t-14-chloro-9α,11α,15S-trihydroxy-prosta-5,13-dien-1-oic acid-11α, 15S-bis-THP-ether, also named as 14-chloro-PGF$_{2α}$ -11,15-bis-THP-ether and of 5c-9α,1-1α,15S-trihydroxy-prost-5-en-13-yn-1-oic acid-11,15-bis-THP-ether also named as 13,14-dehydro-PGF$_{2α}$ - 11,15-bis-THP-ether.

This mixture is absorbed on acid-washed silica (180g) column and eluted with cyclohexane-ethylacetate, to obtain in the following order: 13,14-dehydro-PGF$_{2α}$ -bis-THP-ether (0.21 g), $[α]_D = -18°$ (CHCl$_3$) and 14-chloro-PGF$_{2α}$ -bis-THP ether (0.98 g), $[α]_D = -41.7°$ (CHCl$_3$).

EXAMPLE 34

Under a nitrogen atmosphere, to a stirred solution of 5c,13t-14-chloro-9α,11α,15S-trihydroxy-prosta-5,13-dien-1-oic acid-11,15-bis-THP-ether in dry DMSO (3 ml) is added a solution of potassium tert-butoxide (0.075 g) in dry DMSO (6 ml) and the stirring is continued for 2 hours.

The reaction mixture is then diluted with water (10 ml), acidified to pH 4.5 and extracted repeatedly with ether. The combined organic layers are washed with saturated ammonium sulphate solution till neutral, dried and evaporated to dryness in vacuo to afford 5c-9α,11α,15S-trihydroxy-prost-5-ene-13-yn-1-oic acid-11,15-bis-THP-ether (0.118 g), $[α]_D = -18°$ (CHCl$_3$).

EXAMPLE 35

At 5°–10° C, a solution of triphenyl (4-carboxybutyl) phosphoniumbromide (2.56 g) in dry DMSO (10 ml) is added to a suspension of methyl sulphinyl carbanide obtained starting from 30% NaH (0.35 g) and dry DMSO (10 ml) using the procedure described in Example 33. The deep orange-red solution of the ylid is then treated with 13t-14-chloro-9β,11α,15R-trihydroxy-pentanor-8,12-diiso-prost-13-ene-6-ale-γ-lactol-11,15-bix-DIOX-ether (0.6 g) dissolved in dry DMSO (13 ml). The mixture is stirred only for 12 minutes and then rapidally diluted with water (33 ml).

After extraction with ether until all the triphenyl phosphoxide has been removed, the combined organic layers are re-extracted with 5% sodium bicarbonate.

The pH of the combined aqueous phases is adjusted to pH 4.5–4.7 with 2N–H$_2$SO$_4$, followed by extraction with ether-pentane (1:1).

These organic layer are combined, washed until neutral, dried (Na$_2$SO$_4$) and evaporated to dryness to give 5c,13t-14-chloro-9β,11α,15R-trihydroxy-8,12-diiso-prosta, 5,13-dien-1-oic acid-11α,15R-bis-DIOX-ether (0.55 g), also named as 14-chloro-15-epi-8,12-diiso-PGF$_{2β}$ -11,15R-bis-DIOX-ether.

EXAMPLE 36

Under a nitrogen atmosphere, a stirred suspension of 80% sodium hydride dispersion in mineral oil (1.08 g) in dry DMSO is heated at 60° to give a solution of methyl sulphinyl carbanide in DMSO (about 3 hours).

This stirred mixture, cooled to 5°–10°, is treated with triphenyl-(4-carboxybutyl) phosphonium bromide (7.98 g) in DMSO (24 ml); the deep orange-red solution of the ylid is then treated with 13t-14-chloro-9α,1-1α,15S-trihydroxypentanor-prost-13-ene-6-ale-γ-lactol (0.45 g) in DMSO (20 ml).

After 8 minutes, from the reaction mixture, 26 ml of the red solution are withdrawn, diluted with ice-water (26 ml) and extracted repeatedly with ether until all the triphenyl phosphoxide has been removed. The combined organic layers are re-extracted with 5% NaHCO$_3$; then the pH of the combined aqueous phases is adjusted to pH 4.5–4.7 with 2N–H$_2$SO$_4$, followed by extraction with ether.

These combined organic layers are washed with 10% ammonium sulphate, dried (Na$_2$SO$_4$) and evaporated to dryness in vacuo to afford a crude product (0.15 g) which is absorbed on acid-washed silica (15 g) column.

Following elution with cyclohexane-ethyl acetate (1:1) and with ethyl acetate gives pure 5c,13t-14-chloro-9α, 11α,15S-trihydroxy-prosta-5,13-diene-1-oic acid (0.131 g), $[α]_D = -6.9°$ C (ethanol) also named as 14-chloro-PGF$_{2α}$ . After 12 hours, the remaining portion of the reaction mixture (two-thirds of the initial mixture) is diluted with water (50 ml).

The aqueous phase is extracted with ether to remove the triphenyl phosphoxide and after re-extraction with 0,5N—NaOH, the organic layer is discarded.

The combined alkaline extracts are acidified with 2N—H$_2$SO$_4$ to pH 4, and extracted with ether, the combined organic layers are washed until neutral, dried and evaporated to dryness in vacuo.

Absorption of the residue (310 ml) on acid washed-silica (30 g) column, followed by elution with ethyl acetate affords 5c-9α,11α,15S-trihydroxy-prost-5-en-13-yn-1-oic acid (0.22 g), $[α]_D = +28°$ (ethanol), also named as 13,14-dehydro-PGF$_{2α}$ .

Using the same procedure, the 14-chloro-lactol derivatives of Example 25 are reacted with the Wittig reagent derived from the (4-carboxy butyl)-triphenyl phosphonium bromide to afford the following compounds:

5c,13t-14-chloro-9α,11α,15R-trihydroxy-prosta-5,13-dienoic acid;
5c,13t-14-chloro-16-methyl-9α,11α,15S-trihydroxy-prosta-5,13-dienoic acid;
5c,13t-14-chloro-9α,11α,15S-trihydroxy-20ω-homo-prosta-5,13-dienoic acid;
5c,13t-14-chloro-9α,11α,15R-trihydroxy-20ω-homo-prosta-5,13-dienoic acid;
5c,13-14-chloro-16-methyl-9α,11α,15R-trihydroxy-prosta-5,13-dienoic acid;
5c,13t-14-chloro-9β,11α,15S-trihydroxy-8,12-diiso-prosta-5,13-dienoic acid;
5c,13t-14-chloro-9β,11α,15R-trihydroxy-8,12-diiso-prosta-5,13-dienoic acid;
5c,13t-14-chloro-16-methyl-9β,11α,15S-trihydroxy-8,12-diiso-prosta-5,13-dienoic acid;
5c,13t-14-chloro-16-methyl-9β,11α,15R-trihydroxy-8,12-diiso-prosta-5,13-dienoic acid;
5c,13t-14-chloro-9β,11α,15S-trihydroxy-20ω-homo-8,12-diiso-prosta-5,13-dienoic acid;
5c,13t-14-chloro-9β,11α,15R-trihydroxy-20ω-homo-8,12-diiso-prosta-5,13-dienoic acid;
5c-9α,11α,15R-trihydroxy-prost-5-en-13-ynoic acid;
5cis-9β,11α,15S-trihydroxy-8,12-diiso-prost-5-en-13-ynoic acid;
5cis-16-methyl-9α,11α,15S-trihydroxy-prost-5-en-13-ynoic acid,
5cis-16-methyl-9α,11α,15R-trihydroxy-prost-5-en-13-ynoic acid;

5cis-9α,11α,15S-trihydroxy-20ω-homo-prost-5-en-13-ynoic acid;

5cis-9α,11α,15R-trihydroxy-20ω-homo-prost-5-en-13-ynoic acid;

5cis-9β,11α,15R-trihydroxy-8,12-diiso-prost-5-ene-13-ynoic acid;

5cis-16-methyl-9β,11α,15S-trihydroxy-8,12-diiso-prost-5-ene-13-ynoic acid;

5cis-16-methyl-9β,11α,15R-trihydroxy-8,12-diiso-prost-5-ene-13-ynoic acid;

5cis-9β,11α,15S-trihydroxy-20ω-homo-8,12-diiso-prost-5-ene-13-ynoic acid;

5-cis-9β,11α,15R-trihydroxy-20ω-homo-8,12-diiso-prost-5-ene-13-ynoic acid.

EXAMPLE 37

At −60° C reduction of 9α,11α,15R-trihydroxy-prost-13-yn-6-oic acid-γ-lactone-11α-p-phenylbenzoate (0.82 g) with sodium-bis-2-methoxy ethoxy)-aluminum hydride (3.5 equiv.) affords, after chromatographic purification on silica gel column, the 9α,11α,15R-trihydroxy-prost-13-yn-6-ale-γ-lactol (0.31 g).

Following the procedure described in Example 36, a solution of this compound in DMSO (10 ml), is treated with the ylid solution obtained starting from 5.32 g of (4-carboxy butyl)-triphenyl phosphonium bromide to obtain after chromatographic purification on acid-washed silica (34 g) gel (cyclohexane-ethylacetate 30.70), the 5cis-9α,11α,15R-trihydroxy-prost-5-ene-13-yn-oic acid, $[\alpha]_D = +31.5°$ (ethanol), as a colorless oil (0.27 g).

EXAMPLE 38

Under a nitrogen atmosphere, to a stirred mixture of (β-carboxy-methoxy-ethyl)-triphenylphosphonium bromide (6.15 g) and 13t-14-chloro-9α,11α,15S-trihydroxy-pentanor-prost-13-ene-6-ale-γ-lactol-11α,15S-bis-DIOX-ether (2.6 g) in dry DMSO (32 ml) cooled at 12°–15°, is added a solution of freshly sublimed potassium tert-butoxide (3.05 g) in dry DMSO (42 ml). After an additional stirring for 10 minutes, the reaction mixture is cooled and diluted with water (75 ml).

The aqueous phase is extracted repeatedly with ether to remove the triphenylphosphoxide.

The combined organic layers, after re-extraction with 5% NaHCO₃ solution, are discarded; then the pH of the combined aqueous phases is adjusted to pH 4.5–4.7 with an acid followed by extraction with pentane-ether 1:1.

The combined organic extracts are washed with saturated ammonium sulphate solution until neutral, dried (Na₂SO₄) and evaporated to dryness in vacuo to afford the 5c,13t-14-chloro-9α,11α,15S-trihydroxy-3-oxa-prost-5,13-dienoic acid-11α,15S-bis-DIOX-ether also named as 14-chloro-3-oxa-PGF$_{2\alpha}$-11α,15S-bis-DIOX-ether.

Using this procedure, the 11,15-bis-DIOX-ethers and the 11,15-bis-THP-ethers of the 14-chloro lactols of Example 25, are, reacted with the following triphenylphosphonium bromide derivatives:

(β-carboxymethoxyethyl)triphenylphosphonium bromide;

(β-carboxymethylthioethyl)triphenylphosphonium bromide;

(4-carboxy-but-trans-3-enyl)triphenylphosphonium bromide;

(4-carboxy-but-cis-3-enyl)triphenylphosphonium bromide;

(4-carboxy-but-3-ynyl)triphenylphosphonium bromide;

to afford the following bis-ethers (11α,15-DIOX or 11α,15-THP)-prostadienoic acids, as well as optically acitve or dl- compounds:

5c,13t-14-chloro-9α,11α,15S-trihydroxy-3-oxa-prostadienoic acid;

5c,13t-14-chloro-9α,11α,15S-trihydroxy-3-thia-prostadienoic acid;

2c,5c,13t-14-chloro-9α,11α15S-trihydroxy-prostatrienoic acid;

2t,5c,13t-14-chloro-9α,11α,15S-trihydroxy-prostatrienoic acid;

5c,13t-14-chloro-9α,11α,15S-trihydroxy-prosta-2-yn-5,13-dienoic acid;

5c,13t-14-chloro-9α,11α,15R-trihydroxy-3-oxa-prostadienoic acid;

5c,13t-14-chloro-9α,11α,15R-trihydroxy-3-thia-prostadienoic acid;

2c,5c,13t-14-chloro-9α,11α,15R-trihydroxy-prostatrienoic acid;

2t,5c,13t-14-chloro-9α,11α,15R-trihydroxy-prostatrienoic acid;

5c,13t-14-chloro-9α,11α,15R-trihydroxy-prosta-2-yn-5,13-dienoic acid;

5c,13t-14-chloro-9α,11α,15S-trihydroxy-3-oxa-20ω-homoprostadienoic acid;

5c,13t-14chloro-9α,11α,15R-trihydroxy-3-oxa-20ω-homoprostadienoic acid;

5c,13t-14-chloro-16-methyl-9α,11α,15S-trihydroxy-3-oxaprostadienoic acid;

5c,13t-14-chloro-16-methyl-9α,11α,15R-trihydroxy-3-oxaprostadienoic acid;

5c,13t-14-chloro-9α,11α,15S-trihydroxy-3-oxa-8,12-diiso-prostadienoic acid;

5c,13t-14-chloro-9α,11α,15S-trihydroxy-3-thia-8,12:diiso-prostadienoic acid;

2c,5c,13t-14-chloro-9β,11α,15S-trihydroxy-8,12-diiso-prostatrienoic acid;

2t,5c,13t-14-chloro-9β,11α,15S-trihydroxy-8,12-diiso-prostatrienoic acid;

5c,13t-14-chloro-9β,11α15R-trihydroxy-3-oxa-8,12-diiso-prostadienoic acid;

5c,13t-14-chloro-9β,11α,15R-trihydroxy-3-thia-8,12-diiso-prostdienoic acid;

2c,5c,13t-14-chloro-9β,11α,15R-trihydroxy-8,12-diiso-prostatrienoic acid;

2t,5c,13t-14-chloro-9β,11α,15R-trihydroxy-8,12-diiso-prostatrienoic acid;

5c,13t-14-chloro-9β,11α,15R-trihydroxy-8,12-diiso-prosta-2-yn-5,13-dienoic acid;

5c,13t-14-chloro-9β,11α,15S-trihydroxy-8,12-diiso-prosta-2-yn-5,13-dienoic acid;

5c,13t-14-chloro-9β,11α,15S-trihydroxy-3-oxa-20ω-homo-8,12-diiso-prostadienoic acid;

5c,13t-14-chloro-9β,11α,15R-trihydroxy-3-oxa-20ω-homo-8,12-diiso-prostadienoic acid;

5c,13t-14-chloro-16-methyl-9β,11α,15S-trihydroxy-3-oxa-8,12-diiso-prostadienoic acid;

5c13t-14-chloro-16methyl-9β,11α,15R-trihydroxy-3-oxa-8,12-diiso-prostadienoic acid;

which are optionally converted into their methylesters and then/or deetherified.

EXAMPLE 39

Under a nitrogen atmosphere, to a stirred mixture of 9α,11α,15S-trihydroxy-pentanor-prost-13-yn-6-ale-γ-latol-11α,15S-bis-THP-ether (1.3 g) and of (4-carboxybutyl) triphenylphosphonium bromide (3.8 g) in dry DMSO (16.5 ml), cooled at 15°–18° C, is added potassium tert-butoxide (1.54 g, freshly sublimed) in dry DMSO (20 ml).

After an additional stirring for 12 hours at room temperature the reaction mixtue is diluted with water (40 ml), repeatedly extracted with ether to remove the triphenylphosphoxide.

The combined organic layers are re-extracted with 0.5N sodium hydroxide solution and discarded.

The combined aqueous phases are acidified to pH 4.5–4,7 and re-extracted with a pentane-ether mixture (1:1).

These combined organic extracts are washed with a saturated ammonium sulphate solution until neutral, dried ($Na_2SO_4$) and evaporated to dryness in vacuo to give 5c-9α,11α,15S-trihydroxy-prost-5-en-13-ynoic acid-11α, 15S-bis-THP-ether $[α]_D$= −18° (1.43 g as a colorless oil) also named as 13,14-dehydro-$PGF_{2α}$ - 11α,15S-bis-THP-ether. Following this procedure, the 11,15-bis-THP-ethers and the 11,15-bis-DIOX-ethers of the 13,14-yn-lactols of Examples 31 and 32 are reacted with the (4 carboxybutyl) triphenyl-phosphonium bromide to afford the following bis-esters (11α,15-THP or 11α,15-DIOX)-prost-5-en-13-ynoic acids, as well as optically active or dl-compounds;

5c-9α,11α,15S-trihydroxy-prost-5-ene-13-ynoic acid;
5c,9α,11α,15R-trihydroxy-prost-5-ene-13-ynoic acid;
5c-9α,11α,15S-trihydroxy-20ω-homo-prost-5-ene-13-ynoic acid;
5c-9α,11α,15R-trihydroxy-20ω-homo-prost-5-ene-13-ynoic acid;
5c-16-methyl-9α,11α,15S-trihydroxy-prost-5-ene-13-ynoic acid;
5c-16-methyl-9α,11α,15R-trihydroxy-prost-5-ene-13-ynoic acid;
5c-9α,11α,15S-trihydroxy-8,12-diiso-prost-5-ene-13-ynoic acid;
5c-9β,11α,15R-trihydroxy-8,12-diiso-prost-5-ene-13-ynoic acid;
5c-9β,11α,15S-trihydroxy-20ω-homo-8,12-diiso-prost-5-ene-13-ynoic acid;
5c-9β,11α,15R-trihydroxy-20ω-homo-8,12-diiso-prost-5-ene-13-ynoic acid;
5c-16-methyl-9β,11α,15S-trihydroxy-8,12-diiso-prost-5-ene-13-ynoic acid;
5c-16-methyl-9β,11α,15R-trihydroxy-8,12-diiso-prost-5-ene-13-ynoic acid;

which are optionally deetherified or optionally converted into their methylesters and then deetherified.

EXAMPLE 40

Using the following triphenylphosphonium bromide derivatives (β-carboxy methoxy ethyl-triphenylphosphonium bromide, (β-carboxy methylthio ethyl)-triphenylphosphonium bromide, (4-carboxy-but-trans-3-enyl)-triphenylphosphonium bromide, (4-carboxy-but-cis-3-enyl)-triphenylphosphonium bromide, (4-carboxy-but-3-ynyl)-triphenylphosphonium bromide, in the procedure of Example 39, gives the following bis ethers (11α,15-THP or 11α,15-DIOX)-prost-5-en-13-ynoic acids, as well as optically active or di-compounds:

5c-9α,11α,15S-trihydroxy-3-oxa-prost-5-en-13-ynoic acid;
5c-9α,11α,15S-trihydroxy-3-thia-prost-5-en-13-ynoic acid;
2c,5c-9α,11α,15S-trihydroxy-prosta-2,5-dien-13-ynoic acid;
2t,5c-9α,11α,15S-trihydroxy-prosta-2,5-dien-13-ynoic acid;
5c-9α,11α,15S-trihydroxy-prost-5-en-2,13-diynoic acid;
5c-9α,11α,15R-trihydroxy-3-oxa-prosta-5-en-13-ynoic acid;
5c-9β,11α,15S-trihydroxy-3-oxa-8,12-diiso-prost-5-en-13-ynoic acid;
5c-9β,11α,15R-trihydroxy-3-oxa-8,12-diiso-prost-5-en-13-ynoic acid;
5c-9β,11α,15S-trihydroxy-3-thia-8,12-diiso-prost-5-en-13-ynoic acid;

which are optionally deetherified or optionally converted in their methyl esters and then deetherified.

EXAMPLE 41

Under a nitrogen atmosphere, to a mixture of 13t-14-chloro-9β,11α,15S-trihydroxy-8,12-diiso-prost-13-ene-6-ale-γ-lactol-11,15-bis-DIOX-ether (2.6 g) and of (4-carboxybutyl)-triphenylphosphonium bromide (6.1 g) in dry DMSO (32 ml), by external cooling at 15°–18° C, is added a solution of freshly sublimed potassium tert-butoxide (3.05 g) in dry DMSO (42 ml) over a period of 5 minutes.

After an additional stirring for 15 minutes, the reaction mixture is diluted with water (75 ml) and worked up in usual manner (removal of triphenylphosphoxide with ether, acidification of the alkaline aqueous phases, and following re-extraction with a 1:1 mixture of pentane-ether) to afford the 5c,13t-14-chloro-9β,11α,15S-trihydroxy-8,12-diiso-prostadienoic acid-11α,15S-bis-DIOX-ether (2.7 g), also named as 14-chloro-S,12-diiso-$PGF_{2β}$ -11α,15S-bis-DIOX-ether.

Using the (4-carboxybutyl)-triphenylphosphonium bromide to form the ylid by reaction with potassium tert-butoxide (Example 41) or with methyl sulphinyl carbanide (Example 35) the 11,15-bis-DIOX-ethers and the 11,15-bis-THP-ethers of the 14-chloro lactols of Example 25 are reacted to afford the following bis-ethers (11α,15-DIOX or 11α,15-THP)-prostadienoic acid, as well as optically active or dl-compounds:

5c,13t-14-chloro-9α,15S-trihydroxy-prostadienoic acid;
5c,13t-14-chloro-9α,11α,15R-trihydroxy-prostadienoic acid;
5c,13t-14-chloro-9α,11α,15S-trihydroxy-20ω-homo-prostadienoic acid;
5c,13t-14-chloro-9α,11α,15R-trihydroxy-20ω-homo-prostadienoic acid;
5c,13t-14-chloro-16-methyl-9α,11α,15S-trihydroxy-prostadienoic acid;
5c,13t-14chloro-16-methyl-9α,11α,15R-trihydroxy-prostadienoic acid;
5c,13t-14-chloro-9β,11α,15R-trihydroxy-8,12-diiso-prostadienoic acid;
5c,13t-14chloro-9β,11α,15S-trihydroxy-20ω-homo-8,12-diiso-prostadienoic acid;

5c,13t-14-chloro-9β,11α,15R-trihydroxy-20ω-homo-8,12-diiso-prostadienoic acid;

5c, 13t-14-chloro-16-methyl-9β,11α,15R-trihydroxy-8,1212-diiso-prostadienoic acid;

5c,13t-14-chloro-16-methyl-9β,11α,15S-trihydroxy-8,12-diiso-prostadienoic acid, which are optionally deetherified or optionally converted in their methyl esters and then deetherified.

EXAMPLE 42

Under nitrogen atmosphere, to a stirred mixture of dl-13t-14-chloro-9α,11α,15S-trihydroxy-pentanor-prost-13-en-6-oic acid-γ-lactol 11α,15S-bis-TNP-ether (8.28 g) and of (4-carboxybutyl)-triphenylphosphonium bromide (27.6 g) in dry DMSO (120 ml) cooled at 17°–20° C, is added a solution of potassium tert-butoxide (15.68 g) in dry DMSO (180ml).

The reaction mixture is stirred for 14 hours at room temperature, then diluted with water (300 ml) and worked up in the usual manner to give dl-5-c-9α,11α,15S-trihydroxyprost-5-ene-13-ynoic acid-11α,15-bis-THP-ether(7.95 g). This product (1.95 g) in benzene is treated with ethercal solution of diazomethane (1.25 equiv.) and after 15 minutes the reaction mixture is evaporated to dryness in vacuo to afford the crude methylester (2 g), which is dissolved in acetone (115 ml) and heated with 0.1N aqueous oxalic acid (80 ml) for 12 hours at 40° C.

After removal of the acetone in vacuo the aquous phase is extracted repeatedly with ether, the combined organic layers are washed with saturated ammonium sulphate solution, dried ($Na_2SO_4$) and evaporated in vacuo to dryness to give crude dl-5c-9α,11α,15S-trihydroxy-prost-5-en-13-ynoic acid methylester (1.6 g). This product is absorbed on silica (30 g/g) column and subsequent elution with cyclohexane-ethylacetate (65:35) allows to obtain pure dl-13,14-dehydro-$PGF_{2α}$ -methylester (1.22 g, m.p. 74.5°–75.5° C).

A solution of this compound (0.6 g) in methanol (76 ml)-water (8 ml) is treated with potassium hydroxide (0.4 g) for 2 hours at room temperature, then with saturated sodium dihydrogen phosphate solution to pH 6.4–6.8 and after removal of methanol in vacuo, the reaction mixture is diluted with 0.1N aqueous oxalic acid.

Following extraction with ether and washing to neutrality with saturated ammonium sulphate solution afford, after drying on $Na_2SO_4$ and removal of solvent in vacuo, pure dl-5c-9α,11α,15S-trihydroxy-prost-5-ene-13-ynoic acid (0.52 g, m.p. 80°–82° C).

EXAMPLE 43

Using an excess of the ylid derived from the (4-carboxybutyl)-triphenylphosphonium bromide by means of reaction with freshly sublimed potassium tert-butoxide or with methyl sulphinyl carbanide, the 11α,15-bis ether (11.15-THP and 11,15-DIOX) of 14-chloro-lactols of Example 25 and before, are reacted to give the following bis-ethers (11α,15-THP or 11α,15-DIOX)-prost-5-en-13-ynoic acids, as well as optically active or dl-compounds:

5-cis-9α,11α,15S-trihydroxy-prost-5-ene-13ynoic acid;
5-cis-9α,11α,15R-trihydroxy-prost-5-ene-13-ynoic acid;
5-cis-9α,11α,15S-trihydroxy-20ω-homo-prost-5-ene-13-ynoic acid;
5-cis-9α,11α,15R-trihydroxy-20ω-homo-prost-5-ene-13-ynoic acid;
5-cis-16-metyl-9α,11α,15S-trihydroxy-prost-5-ene-13-ynoic acid;
5-cis-16-methyl-9α,11α,15R-trihydroxy-prost-5-ene-13-ynoic acid;
5-cis-9β,11α,15S-trihydroxy-8,12-diiso-prost-5-ene-13-ynoic acid;
5-cis-9β,11α,15R-trihydroxy-8,12-diiso-prost-5-ene-13-ynoic acid;
5-cis-9β,11α,15S-trihydroxy-20ω-homo-8,12-diiso-prost-5-ene-13-ynoic acid;
5-cis-9β,11α,15R-trihydroxy-20ω-homo-8,12-diiso-prost-5-ene-13-ynoic acid;
5-cis-16-methyl-9β,11α,15S-trihydroxy-8,12-diiso-prost-5-ene-13-ynoic acid;
5-cis-16-methyl-9β,11α,15R-trihydroxy-8,12-diiso-prost-5-ene-13-ynoic acid;

which are optionally deetherified or optionally converted in their methyl esters and then deetherified.

EXAMPLE 44

Using ('β-carboxymethoxyethyl)triphenylphosphonium bromide in the procedure of Example 43 gives:

5c-9α,11α,15S-trihydroxy-3-oxa-prosta-5-ene-13-ynoic acid and its 15R-epimer;
5c-9α,11α,15S-trihydroxy-3-oxa-20ω-homo-prost-5-ene-13-ynoic acid and its 15R-epimer;
5c-9β,11α,15S-trihydroxy-3-oxa-8,12-diiso-prost-5-ene-13-ynoic acid and its 15R-epimer.

Using (β-carboxymethylthioethyl) triphenylphosphonium bromide in the procedure of the Example 43 gives:

5-cis-9α,11α,15S-trihydroxy-3-thia-prost-5-en-13-ynoic acid and its 15R-epimer;
5-cis-9α,11α,15S-trihydroxy-3-thia-20ω-homo-prost-5-en-13ynoic acid and its 15R-epimer;
5-cis-9β,11α,15S-trihydroxy-3-thia-8,12-diiso-prost-5-en-13-ynoic acid and its 15R-epimer.

Using (4-carboxy-but-cis-3-enyl)triphenylphosphonium bromide in the procedure of the Example 43 gives:

2c,5c-9α,11α,15S-trihydroxy-prosta-2,5-dien-13-ynoic acid and its 15R-epimer;
2c,5c-9β,11α,15S-trihydroxy-8,12-diiso-prosta-2,5-dien-13-ynoic acid and its 15R-epimer.

Using (4-carboxy-but-trans-3-enyl)triphenylphosphonium bromide in the procedure of the Example 43 gives:

2t,5c-9α,11α,15S-trihydroxy-prosta-2,5-dien-13-ynoic acid and its 15R-epimer;
2t,5c-9β,11α,15S-trihydroxy-prosta-2,5-dien-13-ynoic acid and its 15R-epimer.

Using (4-carboxy-but-3-ynyl)triphenylphosphonium bromide in the procedure of the example 43 gives:

5c-9α,11α,15S-trihydroxy-prost-5-en-2,13-dyynoic acid and its 15R-epimer;

5c-9β,11α,15S-trihydroxy-8,12-diiso-prost-5-en-2,13-diynoic acid and its 15R-epimer.

All these compounds are optionally deetherified or are optionally converted in their methyl esters and then deetherified.

EXAMPLE 45

A stirred solution of 5c,13t-14-chloro-9α,11α,15S-trihydroxy-prosta-5,13-dienoic acid-11α,15S-bis-THP-ether (1.4 g) in acetone (28 ml), cooled at −18°, is treated with Jones reagent [2.8 ml; prepared by adding concentrated sulphuric acid (61 ml) to chromic anhydride (70 g) in water (500 ml)]. The mixture is stirred at −10° to −12° C for an additional 20 minutes, diluted with benzene (80 ml), washed with saturated ammonium sulphate solution until neutral, dried ($Na_2SO_4$) and the evaporated to dryness in vacuo to yield, as an oil, 5c,13t-14-chloro-11α,15S-dihydroxy-9-oxo-prostadienoic acid-11,15-bis-THP-ether $[\alpha]_D = -82°$ ($CHCl_3$), which is then deetherified in acetone with 0.1N aqueous oxalic acid.

EXAMPLE 46

Using the 5c-9α,11α,15S-trihydroxy-prost-5-en-13-ynoic acid-11,15-bis-THP-ether in the procedure of Example 45 gives 5c-11α,15S-dihydroxy-9-oxo-prost-5-en-13-ynoic acid-11,15-bis-THP-ether, $[\alpha]_D = -82,6°$ ($CHCl_3$).

A solution of this compound (1.4 g) in acetone (200 ml) is treated with 0.1N aqueous oxalic acid (270 ml) at 33° to 37° C for 6 hours; then, after removal of acetone in vacuo, the aqueous phase is repeatedly extracted with ether. The combined organic extracts (250 ml) are washed with saturated ammonium sulphate solution until neutral, dried ($Na_2SO_4$) and evaporated to dryness in vacuo. The residue (1.1 g) is absorbed on an acid washed silica (75 g) column [the acid washed silica gel is prepared by treatment of $SiO_2$ (1 kg) with 2,2 Pt. of 7N—HCl, under stirring for 2 hours, followed by filtration, washing until disappearance of $Cl^-$ ions in the eluate and activation at 120° C under vacuum for 2 days] and eluted with cyclohexane-ethyl acetate mixtures. The eluates from 150–50 cyclohexane-ethyl acetate give, after removal of the solvents in vacuo, the oil 5-cis-11α,15S-dihydroxy-9-oxo-prost-5-en-13-ynoic acid [13,14-dehydro-$PGE_2$] (0.75 g), $[\alpha]_D = -15.1°$ (ethanol). Using the 15R-epimer in this procedure gives the oic 5c-11α,15R-dihydroxy-9-oxo-prost-5-en-13-ynoic acid [13,14-dehydro-15-epi-$PGE_2$], $[\alpha]_D = +31.6°$ (ethanol).

EXAMPLE 47

Starting for the corresponding 9,11,15-trihydroxy-prostanoic acid-11,15-bis-ether (DIOX-ether or THP-ether) or their methyl esters, oxidation with Jones reagent, followed by deetherification give the following (optically active or di-compounds):

5c,13t-14-chloro-11α,15S-dihydroxy-9-oxo-prostadienoic acid;
5c,13t-14-chloro-11α,15R-dihydroxy-9-oxo-prostadienoic acid;
5c,13t-14-chloro-16-methyl-11,α,15S-dihydroxy-9-oxo-prostadienoic acid;
5c,13t-14-chloro-16-methyl-11α,15R-dihydroxy-9-oxo-prostadienoic acid;
5c,13t-14-chloro-16-methyl-11α,15S-dihydroxy-9-oxo-3-oxa-prostadienoic acid;
5c,13t-14-chloro-16-methyl-11α,15R-dihydroxy-9-oxo-3-oxa-prostadienoic acid;
5c,13t-14-chloro-11α,15S-dihydroxy-9-oxo-20ω-homo-prostadienoic acid;
5c,13t-14-chloro-11α,15R-dihydroxy-9-oxo-20ω-homo-prostadienoic acid;
5c,13t-14-chloro-16-methyl-11α,15S-dihydroxy-9-oxo-8,12-diiso-prostadienoic acid;
5c,13t-14-chloro-11α,15S-dihydroxy-9-oxo-8,12-diiso-prostadienoic acid;
5c,13t-14-chloro-11α,15S-dihydroxy-9-oxo-20ω-homo-8,12-diiso-prostadienoic acid;
5c,13t-14-chloro-11α,15S-dihydroxy-9-oxo-20ω-homo-3-oxa-8,12-diiso-prostadienoic acid;
5c,13t-14-chloro-16-methyl-11α,15R-dihydroxy-9-oxo-8,12-diiso-prostadienoic acid;
5c,13t-14-chloro-11α,15R-dihydroxy-9-oxo-8,12-diiso-prostadienoic acid;
5c,13t-14-chloro-11α,15R-dihydroxy-9-oxo-20ω-homo-8,12-diiso-prostadienoic acid;
5c,13t-14-chloro-11α,15R-dihydroxy-9-oxo-20ω-homo-3-oxa-8,12-prostadienoic acid;
5c,13t-14-chloro-11α,15S-dihydroxy-9-oxo-3-oxa-prostadienoic acid;
5c,13t-14-chloro-11α,15S-dihydroxy-9-oxo-3-oxa-prostadienoic acid;
5c,13t-14-chloro-11α,15S-dihydroxy-9-oxo-3-oxa-8,12-diiso-prostadienoic acid;
5c,13t-14-chloro-11α,15R-dihydroxy-9-oxo-3-oxa-8,12-diiso-prostadienoic acid;
5c,11α,15S-dihydroxy-9-oxo-prosten-13-ynoic acid;
5c-11α,15R-dihydroxy-9-oxo-prosten-13ynoic acid;
5c-11α,15S-dihydroxy-9-oxo-20ω-homo-prosten-13-ynoic acid
5c-16-methyl-11α,15S-dihydroxy-9-oxo-prosten-13-ynoic acid;
5c-11α,15S-dihydroxy-9-oxa-prosten-13-ynoic acid;
5c-11α,15S-dihydroxy-9-oxo-3-oxa-20ω-homo-prosten-13-ynoic acid;
5c-16-methyl-11α,15R-dihydroxy-9-oxo-prosten-13-ynoic acid;
5c-11α,15R-dihydroxy-9-oxo-20ω-homo-prosten-13-ynoic acid;
5c-11α,15R-dihydroxy-9-oxo-3-oxa-20ω-homo-prosten-13-ynoic acid;
5c-16-methyl-11α,15R-dihydroxy-9-oxo-3-oxa-prosten-13-ynoic acid;
5c-11α,15R-dihydroxy-9-oxo-3-oxa-prosten-13-ynoic acid;
5c-11α,15S-dihydroxy-9-oxo-8,12-diiso-prosten-13-ynoic acid;
5c-16-methyl-11α,15S-dihydroxy-9-oxo-8,12-diiso-prosten-13-ynoic acid;
5c-11α,15S-dihydroxy-9-oxo-20ω-homo-8,12-diiso-prosten-13-ynoic acid;
5c-11α,15S-dihydroxy-9-oxo-3-oxa-8,12-diiso-prosten-13-ynoic acid;
5c-16-methyl-11α,15S-dihydroxy-9-oxo-3-oxa-8,12-diiso-prosten-13-ynoic acid;
5c-11α,15S-dihydroxy-9-oxo-3-oxa-20ω-homo-8,12-diiso-prosten-13-ynoic acid;
5c-11α,15R-dihydroxy-9-oxo-8,12-diiso-prosten-13-ynoic acid;
5c-16-methyl-11α,15R-dihydroxy-9-oxo-8,12-diiso-prosten-13-ynoic acid;

5c-11α,15R-dihydroxy-9-oxo-20ω-homo-8,12-diiso-prosten-13-ynoic acid;

5c-11α,15R-dihydroxy-9-oxo-3-oxa-8,12-diiso-prosten-13-ynoic acid;

5c-11α,15R-dihydroxy-9-oxo-3-oxa-20ω-homo-8,12-diiso-prosten-13-ynoic acid;

5c-16-methyl-11α,15R-dihydroxy-9-oxo-3-oxa-8,12-diiso-prosten-13-ynoic acid;

EXAMPLE 48

A solution of dl-5c,13t-14-chloro-9α,11α,15S-trihydroxyprostadienoic acid-11α,15S-bis-THP (0.228 g) in pyridine (0.6 ml) is treated with acetic anhydride (0.2 ml) at room temperature. After 12 hours the mixture is poured in 20% aqueous citric acid (10 ml) and extracted repeatedly with ether (80 ml). The combined organic phases are washed with 2N citric acid, water and a saturated ammonium sulphate solution until neutral, dried ($Na_2SO_4$) and evaporated to dryness in vacuo to afford dl-5c,13t-9α,11α,15-trihydroxy-prostadienoic acid-11α,15S-bis-THP-ether-9-acetate (0.22 g). A solution of this compound in acetone (24 ml) is treated with 0,2N aqueous citric acid and heated for 20 hours at 38°–40° C; after removal of acetone in vacuo, the reaction mixture is extracted with ether.

The combined organic extracts are washed up to neutrality dried and evaporated to dryness in vacuo to afford a crude product (0.18 g). The residue is adsorbed on an acid washed silica (1.4 g) column and eluted with cyclohexane-ethyl acetate mixtures.

The eluates from 150/50 cyclohexane-ethylacetate give, after removal of the solvents in vacuo, the oil dl-5c, 13t-14-chloro- 9α,11α,15S-trihydroxy-prostadienoic acid-9-acetate. Starting from the corresponding 9,11α,15-trihydroxy-11α,15-bis-acetalic ethers, treatment in pyridine with a convenient anhydride or with a convenient chloride of a carboxylic acid, followed deetherification, gives the following:

5c,13t-14-chloro-9α,11α,15S-trihydroxy-prostadienoic acid-9-propionate;

5c,13t-14-chloro-9α,11α,15S-trihydroxy-prostadienoic acid-9-p-phenylbenzoate;

5c,13t-14-chloro-9α,11α,15S-trihydroxy-prostadienoic acid-9-benzoate;

5c-9α,11α,15S-trihydroxy-prosten-13-ynoic acid-9-acetate;

5c-9α,11α,15S-trihydroxy-prosten-13-ynoic acid-9-p-phenylbenzoate;

5c-9α,11α,15S-trihydroxy-prosten-13-ynoic acid-9-propionate;

5c-9α,11α,15S-trihydroxy-prosten-13-ynoic acid-9-benzoate;

5c,13t-14-chloro-16-methyl-9α,11α,15S-trihydroxy-prostadienoic acid-9-acetate;

5c,13t-14-chloro-16-methyl-9α,11α,15S-trihydroxy-prostadienoic acid-9-p-phenylbenzoate;

5c,13t-14-chloro-16-methyl-9α,11α,15S-trihydroxy-prostadienoic acid-9-benzoate;

5c,13t-14-chloro-16-methyl-9α,11α,15S-trihydroxy-prostadienoic acid-9-propionate;

5c-9α,11α,15S-trihydroxy-prosten-13-ynoic acid-9-acetate;

5c-9α,11α,15S-trihydroxy-prosten-13-ynoic acid-9-p-phenylbenzoate;

5c-9α,11α,15S-trihydroxy-prosten-13-ynoic acid-9-benzoate;

5c-9α,11α,15S-trihydroxy-prosten-13-ynoic acid-9-propionate.

EXMPLE 49

A stirred solution of 5c,13t-14-chloro-9β,11α,15S-trihydroxy-8,12-diiso-prostadienoic acid-11α,15S-bis-DIOX-ether (2.4 g) in acetone (48 ml), cooled at −20° C, is treated with Jones reagent (4.8 ml).

The mixture is stirred at −20° to −10° C for an additional 25 minutes, diluted with benzene (160 ml) and washed repeatedly with a saturated ammonium sulphate solution (10 × 15 ml) until neutral; aqueous washing are re-extracted with benzene and the combined organic layers are dried ($Na_2SO_4$), evaporated to dryness in vacuo to give 5c,13t-14-chloro-11α,15S-dihydroxy-9-oxo-8,12-diiso-prostadienoic acid-11α,15S-bis-DIOX-ether (2.4 g).

A solution of this product in acetone (100 ml) is treated with 0.1N-aqueous oxalic acid for 5 hours at 38° C, and then, after removal of acetone in vacuo, the aqueous phase is extracted with ether (5 × 20 ml).

The combined organic layer is washed with a saturated ammonium sulphate solution until neutral, dried and evaporated to dryness to give a crude product, which is adsorbed on acid washed-silica (150 g) column.

Elution with elthylacetate-cyclohexane (1:1), after removal of solvents in vacuo, gives pure 5c,13t-14-chloro-11α,15S-dihydroxy-9-oxo-8,12-diiso-prostadienoic acid also named as 14-chloro-8,12-diiso-$PGE_2$ (0.92 g).

EXAMPLE 50

An ethereal solution of 5c,13t-14-chloro-9β,11α,15S-trihydroxy-8,12-diiso-prostadienoic acid-11,15-bis-DIOX-ether is treated at room temperature, with a diazoalkane (e.g. diazomethane) solution (1.2 equiv.). After 30 minutes, the mixture is evaporated to dryness in vacuo to afford 5c,13t-14-chloro-9β,11α,15S-trihydroxy-8,12-diiso-prostadienoic acid-11,15-bis-DIOX-ether-methyl ester.

Using this procedure, we prepare the methyl esters and the ethyl esters of the 14-chloro-prestadienoic acid as well as of the prosten-13-ynoic acid.

EXAMPLE 51

To a solution of 5c-9α,11α,15S-trihydroxy-prosten-13-ynoic acid-11α,15S-bis-DIOX-ether in pyridine (2.75 ml) and methylene chloride (27 ml) are added n-octanol (0.9 g) and cyclohexylcarbodiimide (0.5 g). After 2½ hours, the reaction mixture is filtered, concentrated in vacuo to a small volume and the adsorbed on a silica column. Subsequent elution with cyclohexane-ethylacetate-pyridine (800:200:5) affords pure 5c-9α,11α,15S-trihydroxy-prosten-13-ynois acid-octyl ester-11α,15S-bis-DIOX-ether (0.96 g).

A solution of this compound in acetone (50 ml), after addition of 0.1N aqueous oxalic acid (40 ml) is warmed for 12 hours at 35°–40°. After removal of acetone in vacuo and extraction of aqueous phase with ether, the combined ethereal extracts are washed with saturated sodium chloride solution, dried ($Na_2SO_4$) and evaporated to dryness in vacuo, to give after chromatographic purification on silica column [elution with cyclohexane-ethylacetate 7:3], pure 5c-9α,11α,15S-trihydroxy-prosten-13-ynoic acid-n-octil ester.

Starting from the corresponding 5c,13t-14-chloro-trihydroxyprosta-dienoic-11,15-bis-ether, as, from the corresponding 5c-trihydroxy-prosten-13-ynoic acid-11,15-bis-ether and working up as above described, by esterification with a convenient alcohol optionally followed by deetherification, we prepare the esters [11,15-bis-ether-(11,15-DIOX-ether and 11,15-THP-ether) and 11,15-free alcohols] of the following compounds:

5c-9α,11α,15S-trihydroxy-prosten-13-ynoic acid-trichloroethyl ester;
5c-9α,11α,15S-trihydroxy-prosten-13-ynoic acid-n-decylester;
5c-9α,11α,15S-trihydroxy-prosten-13-prosten-13-ynoic acid-n-octadecyl ester;
5c-9α,11α,15S-trihydroxy-prosten-13-ynoic acid-n-dodecyl ester;
5c-9α,11α,15S-trihydroxy-prosten-13-ynoic acid-n-hexyl ester;
5c-9α,11α,15S-trihydroxy-20ω-homo-prosten-13-ynoic acid-n-octyl ester;
5c-9α,11α,15S-trihydroxy-20ω-homo-prosten-13-ynoic acid-n-decyl ester;
5c-9α,11α,15S-trihydroxy-20ω-homo-prosten-13-ynoic acid-n-octadecyl ester;
5c-9α,11α,15S-trihydroxy-20ω-homo-prosten-13-ynoic acid-trichloroesthyl ester;
5c-9α,11α,15S-trihydroxy-20ω-homo-prosten-13-ynoic acid-n-hexyl ester;
5c-16-methyl-9α,11α,15S-trihydroxy-prosten-13-ynoic acid-n-octyl ester;
5c-16-methyl-9α,11α,15S-trihydroxy-posten-13-ynoic acid-n-decyl ester;
5c-16-methyl-9α,11α,15S-trihydroxy-prosten-13-ynoic acid-n-octadecyl ester;
5c-16-methyl-9α,11α,15S-trihydroxy-prosten-13-ynoic acid-n-hexyl ester;
5c-16-methyl-9α,11α,15S-trihydroxy-prosten-13-ynoic acid-n-trichloroethyl ester;
5c,13t-14-chloro-9α,11α,15S-trihydroxy-prostadienoic acid-trichloroethyl ester;
5c,13t-14-chloro-9α,11α,15S-trihydroxy-prostadienoic acid-n-octyl ester;
5c,13t-14-chloro-9α,11α,15S-trihydroxy-prostadienoic acid-n-hexyl ester;
5c,13t-14-chloro-9α,11α,15S-trihydroxy-prostadienoic acid-n-decyl ester;
5c,13t-14-chloro-9α,11α,15S-trihydroxy-prostadienoic acid-n-dodecyl ester;
5c,13t-14-chloro-9α,11α,15S-trihydroxy-prostadienoic acid-n-octadecyl ester;
5c,13t-14-chloro-9α,11α,15S-trihydroxy-20ω-homo-prostadienoic acid-trichloroethyl ester;
5c,13t-14-chloro-9α,11α,15S-trihydroxy-20ω-homo-prostadienoic acid-n-hexyl ester;
5c,13t-14-chloro-9α,11α,15S-trihydroxy-20ω-homo-prostadienoic acid-n-octyl ester;
5c,13t-14-chloro-9α,11α,15S-trihydroxy-20ω-homo-prostadienoic acid-n-decyl ester;
5c,13t-14-chloro-9α,11α,15S-trihydroxy-20ω-homo-prostadienoci acid-n-dodecyl ester;
5c,13t-14-chloro-9α,11α,15S-trihydroxy-20ω-homo-protadienoic acid-n-octadecyl ester;
5c,13t-14-chloro-16-methyl-9α,11α,15S-trihydroxy-prostadienoic acid-trichloroethyl ester;
5c,13t-14-chloro-16-methyl-9α,11α,15S-trihydroxy-prostadienoic acid-n-hexyl ester;
5c,13t-14-chloro-16-methyl-9α,11α,15S-trihydroxy-prostadienoic acid-n-octyl ester;
5c,13t-14-chloro-16-methyl-9α,11α,15S-trihydroxy-prostadienoic acid-n-decyl ester;
5c,13t-14-chloro-16-methyl-9α,11α,15S-trihydroxy-prostadienoic acid-n-octadecyl ester;
5c-9β,11α,15S-trihydroxy-8,12-diiso-prosten-13-ynoic acid-trichloroethyl ester;
5c-9β,11α,15S-trihydroxy-8,12-diiso-prosten-13-ynoic acid-n-hexyl ester;
5c-9β,11α,15S-trihydroxy-8,12-diiso-prosten-13-ynoic acid-n-octyl ester;
5c-9β,11α,15S-trihydroxy-8,12-diiso-prosten-13-ynoic acid-n-decyl ester;
5c-9β,11α,15S-trihydroxy-8,12-diiso-prosten-13-ynoic acid-n-octadecyl ester;
5c-9β,11α,15S-trihydroxy-20ω-homo-8,12-diiso-prosten-13-ynoic acid-trichloroethyl ester;
5c-9β,11α,15S-trihydroxy-20ω-homo-8,12-diiso-prosten-13-ynoic acid-n-hexyl ester;
5c-9β,11α,15S-trihydroxy-20ω-homo-8,12-diiso-prosten-13-ynoic acid-n-octyl ester;
5c-9β,11α,15S-trihydroxy-20ω-homo-8,12-diiso-prosten-13-ynoic acid-n-decyl ester;
5c-9β,11α,15S-trihydroxy-20ω-homo-8,12-diiso-prosten-13-ynoic acid-n-octadecyl ester;
5c-16-methyl-9β,11α,15S-trihydroxy-8,12-diiso-prosten-13-ynoic acid-trichloroethyl ester;
5c-16-methyl-9β,11α,15S-trihydroxy-8,12-diiso-prosten-13-ynoic acid-n-hexyl ester;
5c-16-methyl-9β,11α,15S-trihydroxy-8,12-diiso-prosten-13-ynoic acid-n-octyl ester;
5c-16-methyl-9β,11α,15S-trihydroxy-8,12-diiso-prosten-13-ynoic acid-n-decyl ester;
5c-16-methyl-9β,11α,15S-trihydroxy-8,12-diiso-prosten-13-ynoic acid-n-octadecyl ester;
5c,13t-14-chloro-9β,11α,15S-trihydroxy-8,12-diiso-prosta-dienoic acid-trichloroethyl ester;
5c,13t-14-chloro-9β,11α,15S-trihydroxy-8,12-diiso-prostadienoic acid-n-hexyl ester;
5c,13t-14-chloro-9β,11α,15S-trihydroxy-8,12-diiso-prostadienoic acid-n-octyl ester;
5c,13t-14-chloro-9β,11α,15S-trihydroxy-8,12-diiso-prostadienoic acid-n-decyl ester;
5c,13t-14-chloro-9β,11α,15S-trihydroxy-8,12-diiso-prostadienoic acid-n-octadecyl ester;
5c,13t-14-chloro-9β,11α,15S-trihydroxy-20ω-homo-8,12-diisoprostadienoic acid-trichloroethyl ester;
5c,13t-14-chloro-9β,11α,15S-trihydroxy-20ω-homo-8,12-diiso-prostadienoic acid-n-hexyl ester;
5c,13t-14-chloro-9β,11α,15S-trihydroxy-20ω-homo-8,12-diiso-prostadienoic acid-n-octyl ester;
5c,13t-14-chloro-9β,11α,15S-trihydroxy-20ω-homo-8,12-diiso-prostadienoic acid-n-decyl ester;
5c,13t-14-chloro-9β,11α,15S-trihydroxy-20ω-homo-8,12-diiso-prostadienoic acid-n-octadecyl ester;
5c,13t-14-chloro-16-methyl-9β,11α,15S-trihydroxy-8,12-diiso-prostadienoic acid-trichioroethyl ester;
5c,13t-14-chloro-16-methyl-9β,11α,15S-trihydroxy-8,12-diiso-prostadienoic acid-n-hexyl ester;
5c,13t-14-chloro-16-methyl-9β,11α,15S-trihydroxy-8,12-diiso-prostadienoic acid-n-octyl ester;
5c,13t-14-chloro-16-methyl-9β,11α,15S-trihydroxy-8,12-diisoprostadienoic acid-n-decyl ester;
5c,13t-14-chloro-16-methyl-9β,11α,15S-trihydroxy-8,12-disso-prostadienoic acid-n-octadecyl ester.

EXAMPLE 52

A stirred solution of 5c-9α,11α,15S-trihydroxy-prosten-13-ynoic acid-octyl ester-11α,15S-bis-DIOX-ether (0.67 g) in acetone, cooled at −20°, is treated with Jones reagent (1.25 ml). The mixture is stirred at −20° to −10° C for 15 minutes, diluted with benzene and washed with a saturated ammonium sulphate solution until neutral, dried ($Na_2SO_4$) and evaporated to dryness in vacuo to afford the 5c-11α,15S-dihydroxy-9-oxo-prosten-13-ynoic acid-n-octyl ester-11α,15S-bis-DIOX-ether (0.62 g).

A solution of this compound in acetone-0.1N aqueous oxalic acid (1:1) is warmed for 6 hours at 33°–38°; after removal of acetone in vacuo, the aqueous phase is extracted with ether. The combined organic layers are washed up to neutrality, dried ($Na_2SO_4$) and evaporated to dryness in vacuo. The residue is adsorbed on silica gel column and eluted with cyclohexane-ethyl acetate (8:2) to afford, after removal of solvents in vacuo, 5c-11α,15S-dihydroxy-9-oxo-prosten-13-ynoic acid-n-octyl ester.

Starting from the corresponding esters (methyl, ethyl, tri-chloroethyl, n-hexyl-, n-octyl-, n-decyl-, n-dodecyl-) of the 11,15-bis-ether (11,15-DIOX and 11,15-THP) of the prostenoic acid, prepared as described in Examples 50, 51 oxidation with Jones reagent affords the corresponding esters (methyl, ethyl, trichloroethyl, n-hexyl-, n-octyl-, n-decyl-, n-dodecyl-)-11,15-bis-ether (11,15-DIOX; 11,15-THP), which are optionally deetherified, of the following 9-oxo-derivatives:

5c,13t-14-chloro-11α,15S-dihydroxy-9-oxo-prostadienoic acid;
5c,13t-14-chloro-11α,15R-dihydroxy-9-oxo-prostadienoic acid;
5c,13t-14-chloro-11α,15S-dihydroxy-9-oxo-20ω-homo-prostadienoic acid;
5c,13t-14-chloro-11α,15R-dihydroxy-9-oxo-20ω-homo-prosta-dienoic acid;
5c,13t-14-chloro-16-methyl-11α,15S-dihydroxy-9-oxo-prosta-dienoic acid;
5c,13t-14-chloro-16-methyl-11α,15R-dihydroxy-9-oxo-prosta-dienoic acid;
5c-11α,15S-dihydroxy-9-oxo-prosten-13-ynoic acid;
5c-11α,15R-dihydroxy-9-oxo-prosten-13-ynoic acid;
5c-11α,15S-dihydroxy-9-oxo-20ω-homo-prosten-13-ynoic acid;
5c-11α,15R-dihydroxy-9-oxo-20ω-homo-prosten-13-ynoic acid;
5c-16-methyl-11α,15S-dihydroxy-9-oxo-prosten-13-ynoic acid;
5c-16-methyl-11α,15R-dihydroxy-9-oxo-prosten-13-ynoic acid;
5c,13t-14-chloro-11α,15S-dihydroxy-9-oxo-8,12-diiso-prosta-dienoic acid;
5c,13t-14-chloro-11α,15R-dihydroxy-9-oxo-8,12-diiso-prosta-dienoic acid;
5c,13t-14-chloro-16-methyl-11α,15S-dihydroxy-9-oxo-8,12-diiso-prostadienoic acid;
5c,13t-14-chloro-16-methyl-11α,15R-dihydroxy-9-oxo-8,12-diiso-prostadienoic acid;
5c,13t-14-chloro-11α,15S-dihydroxy-9-oxo-20ω-homo-8,12-diiso-prostadienoic acid;
5c,13t-14chloro-11α,15R-dihydroxy-9-oxo-20ω-homo-8,12-diiso-prostadienoic acid;
5c-11α,15S-dihydroxy-9-oxo-8,12-diiso-prosten-13-ynoic acid;
5c-11α,15R-dihydroxy-9-oxo-8,12-diiso-prosten-13-ynoic acid;
5c-11α,15S-dihydroxy-9-oxo-20ω-homo-8,12-diisoprosten-13-ynoic acid;
5c-11α,15R-dihydroxy-9-oxo-20ω-homo-8,12-diisoprosten-13-ynoic acid;
5c-16-methyl-11α,15S-dihydroxy-9-oxo-8,12-diisoprosten-13-ynoic acid;
5c-16-methyl-11α,15R-dihydroxy-9-oxo-8,12-diisoprosten-13-ynoic acid.

EXAMPLE 53

A stirred solution of 5c-11α,15S-dihydroxy-9-oxo-8,12-diisoprosten-13-ynoic acid-methylester-11α,15S-bis-THP-ether (0.54 g) in methanol-methylene chloride (1:1) (20 ml), cooled at 0° C, is treated with sodium borohydride (50 mg) and the stirring is continued for an additional 30 minutes; then the excess reagent is destroyed by addition of few drops of acetone and the mixture is concentrated in vacuo to small volume. After dilution with ether, the organic layer is washed until neutral with 10% ammonium sulphate solution, dried ($Na_2SO_4$) and evaporated to dryness in vacuo to give 5c-9α,11α,15S-trihydroxy-8,12-diiso-prosten-13-ynoic acid-methyl ester-11,15-bis-THP-ether (0.5 g), which is deetherified by treatment with acetone (24 ml) and 0.2N-aqueous citric acid (30 ml) for 20 hours at 38°–40° C.

After removal of acetone in vacuo, the aqueous phase is repeatedly extracted with ether, the combined organic layers are washed with 15% $(NH_4)_2SO_4$ solution until neutral, dried ($Na_2SO_4$) and evaporated to dryness in vacuo to give a crude product (0.46 g) which is purified by elution on a silica column with cyclohexane-ethyl acetate mixtures. The eluates (from cyclohexane-ethylacetate 1:1), after removal of solvents in vacuo, give pure 5c-9α,11α,15S-trihydroxy-8,12-diiso-prosten-13-ynoic acid-methyl ester (0.28 g).

A solution of this compound (0.12 g) in methanol is treated with 2N sodium hydroxide (2 equiv.) refluxed for 30 minutes, concentrated in vacuo to small volume and diluted with water. The aqueous phase is extracted with ether, the combined organic layers after re-extraction with 0.5N sodium hydroxy are descarded. The pH of the combined alkaline layers is adjusted to pH 4.5–4.6, followed by extraction with ether. These combined organic phases are washed with saturated $(NH_4)_2SO_4$ solution until neutral, dried ($Na_2SO_4$) and evaporated to dryness to afford pure 5c-9α,11α,15S-trihydroxy-8,12-diiso-prosten-13-ynoic acid (0.068) as a colorless oil.

EXAMPLE 54

Using the procedure of Example 53, the 14-chloro-9-oxo-8,12-diiso-prostadienoic ester-11,15-bis-ether derivatives as the 9-oxo-8,12-diiso-prosten-13-ynoic ester-11,15-bis ether derivatives of Example 52, are reacted with sodium borohydride to afford, after deetherification the esters (methyl, ethyl, trichloroethyl, octyl, n-hexyl-, n-decyl-, n-dodecyl-) and after optional saponification the free acids of the following compounds:

5c-9α,11α,15S-trihydroxy-8,12-diiso-prosten-13-ynoic acid;
5c-9α,11α,15S-trihydroxy-20ω-homo-8,12-diiso-prosten-13-ynoic acid;
5c-16-methyl-9α,11α,15S-trihydroxy-8,12-diiso-prosten-13-ynoic acid;

5c,13t-14-chloro-9α,11α,15S-trihydroxy-8,12-diiso-prostadienoic acid;

5c,13t-16-methyl-14-chloro-9α,11α,15S-trihydroxy-8,12diiso-prostadienoic acid;

5c,13t-14-chloro-9α,11α,15S-trihydroxy-20ω-homo-8,12-diiso-prostadienoic acid.

EXAMPLE 55

A stirred solution of 5c,13t-14-chloro-11α,15S-dihydroxy-9-oxo-prostadienoic acid methylester-11,15-bis-THP (0.89) in 20 ml of methanol-methylene chloride (1:1) is reacted with sodium borohydride (100 mg). After an additional stirring for 30 minutes, the excess reagent is destroyed by addition of few drops of actone. The mixture is concentrated to small volume in vacuo, diluted with ether-methylene chloride (5:1) washed with 10% $(NH_4)_2SO_4$ solution until neutral and dried $(Na_2SO_4)$. After removal of solvents in vacuo, the residue is absorbed on silica (100 g) column and eluted with cyclohexane-other mixtures to obtain in order: 14-chloro-$PGF_{2\alpha}$ -methylester-11,15-bis-THP-ether (0.2 g) and 5c,13t-14-chloro-9β,11α,15S-trihydroxy-prostadienoic acid methylester-11,15-bis-THP-ether (0.39 g).

This product is deetherified by treatment with acetone (20 ml) and 0.2N citric acid (15 ml) for 12 hours at 38°–40° to afford 5c,13t-14-chloro-9β,11α,15S-trihydroxy-prostadienoic acid methylester (0.2 g).

At the end, this methylester is reacted in methanol with 0.1 potassium hydroxide (2 equiv.) at reflux temperature for 30 minutes to give 5c,13t-14-chloro-9β,11α,15S-trihydroxy-prostadienoic acid (0.08 g) also named as 14-chloro-$PGF_{2\beta}$ .

EXAMPLE 56

Using the procedure of Example 55, the 14-chloro-9-oxo-prostadienoic ester-11,15-bis-ether derivatives as the 9-oxo-prosten-13-ynoic acid ester-11,15-bis-ether derivatives of Example 52, are reacted with sodium borohydride to afford after deetherification the esters (methyl, ethyl, trichloroethyl, n-hexyl, n-octyl, n-decyl, n-dodecyl) and after optional saponification the free acids of the following compounds:

5c,13t-11-chloro-9β,11α,15S-trihydroxy-prostadienoic acid;

5c,13t-14-chloro-16-methyl-9β,11α,15S-trihydroxy-prostadienoic acid;

5c,13t-14-chloro-9β,11α,15S-trihydroxy-2-homo-prostadienoic acid;

5c,9β,11α,15S-trihydroxy-prosten-13-ynoic acid;

5c-16-methyl-9β,11α,15S-trihydroxy-prosten-13-ynoic acid;

5c-9β, 11α,15S-trihydroxy-20ω-homo-prosten-13-ynoic acid.

EXAMPLE 57

A solution of dl-5c,13t-14-chloro-11α,15S-dihydroxy-9-oxo-prostadienoic acid-11,15-bis-THP-ether (also named as dl-14-chloro-$PGE_2$-11,15-bis-THP-ether) in acetone (40 ml) is treated with 0.2N-oxalic acid (51 ml) and warmed for 6 hours at 60°–65° C. After removal of acetone in vacuo, the aqueous phase is repeatedly extracted with ether; the combined organic layers are washed with saturated $(NH_4)_2SO_4$ solution until neutral, dried $(Na_2SO_4)$. After removal of solvents, the residue is purified by preparative T.L.C. on silica platts using mixture of benzene-ethyl acetate-acetic acid (130:24:12) as eluent, to obtain dl-5c,13t-14-chloro-15S-hydroxy-9oxo-prosta-5,10,12-trienoic acid (0.12 g) also named as dl-14-chloro-$PGA_2$.

EXAMPLE 58

Using the procedure of Example 57, the 14-chloro-9-oxo-prostadienoic acid-11,15-bis-ethers of Examples 45 and 47 and their esters of Examples 52 are deetherified at 60°–65° with acetone-0.2N aqueous oxalic acid to afford the esters (methyl, ethyl, trichleroethyl, n-hexyl, n-octyl-, n-decyl-, n-dodecyl-) and the free acids of the following optically active and dl-compounds:

5c,13t-14-chloro-15S-hydroxy-9-oxo-prosta-5,10,12-trienoic acid and its 15R-epimer;

5c,13t-14-chloro-15S-hydroxy-9-oxo-20ω-homo-prosto-5,10,13-trienoic acid and its 15R-epimer;

5c,13t-14-chloro-16-methyl-15S-hydroxy-9-oxo-prosta-5,10,13-trienoic acid and its 15R-epimer;

5c,13t-14-chloro-15S-hydroxy-9-oxo-3-homo-prosta-5,10,13-trienoic acid and its 15R-epimer;

2c,5c,13t-chloro-15S-hydroxy-9-oxo-prosta-2,5,10,13-tetraenoic acid and its 15R-epimer;

2t,5c,13t-14-chloro-15S-hydroxy-9-oxo-prosta-2,5,10,13-tetraenoic acid and its 15R-epimer;

5c,13t-14-chloro-15S-hydroxy-9-oxo-prosta-5,10,13-trien-2-yn-oic acid and its 15R-epimer;

5c,13t-14-chloro-15S-hydroxy-9-oxo-8,12-diiso-prosta-5,10,13-trienoic acid and its 15R-epimer;

5c,13t-14-chloro-15S-hydroxy-9-oxo-3-oxa-8,12-diiso-prosta-5,10,13-trienoic acid and its 15R-epimer;

5c,13t-14-chloro-16-methyl-15S-hydroxy-9oxo-8,12-diiso-prosta-5,10,13-trienoic acid and its 15R-epimer;

5c,13t-14-chloro-15S-hydroxy-9-oxo-20ω-homo-8,12-diiso-prosta-5,10,13-trienoic acid and its 15R-epimer.

EXAMPLE 59

A solution of 5c-16-methyl-11α,15S-dihydroxy-9-oxo-prosten-13-ynoic acid-n-octyl ester-11,15-bis-DIOX-ether (0.6 g) in acetone (45 ml) and 0.25 N aqueous oxalic acid (54 ml) is warmed at 60°–65° for 6 hours and after removal of acetone in vacuo, the aqueous phase is repeatedly extracted with ether-methylene chloride 5:1. The combined organic layers are washed with a saturated $(NH_4)_2SO_4$ solution until neutral, dried on $Na_2SO_4$ and evaporated to dryness. The residue is purified by preparative TLC chromatography (eluent cyclohexane-ether) to give the 5c-16-methyl-15S-hydroxy-9-oxo-prosta-5,10-dien-13-ynoic acid-N-octyl ester (0.25 g).

EXAMPLE 60

Using the procedure of Example 59, the 9-oxo-prosten-13-ynoic acid-11,15-bis-ethers of Examples 46 and 47 and their esters of Example 52 are deetherified at 60°–65° with acetone-0.25N aqueous oxalic acid to afford the esters (methyl, ethyl, trichloroethyl, n-hexyl-, n-octyl-, n-decyl-, n-dodecyl-) and the free acids of the following optically active and dl-compounds:

5c-15S-hydroxy-9-oxo-prosta-5,10-dien-13-ynoic acid and its 15R-epimer;

5c-15S-hydroxy-9-oxo-20ω-homo-prosta-5,10-dien-13-ynoic acid and its 15R-epimer;

5c-16-methyl-15S-hydroxy-9-oxo-prosta-5,10-dien-13-ynoic acid and its 15R-epimer;

5c-15S-hydroxy-9-oxo-8,12-diiso-prosta-5,10-dien-13-ynoic acid and its 15R-epimer;

5c-15S-hydroxy-9-oxo-20ω-homo-3,12-diiso-prosta-5,10-dien-13-ynoic acid and its 15R-epimer;

5c-16-methyl-15S-hydroxy-9-oxo-8,12-diiso-prosta-5,10-dien-13-ynoic acid and its 15R-epimer;

5c-15S-hydroxy-9-oxo-3-oxa-8,12-diiso-prosta-5,10-dien-13-ynoic acid and its 15R-epimer;

5c-15-hydroxy-9-oxo-3-oxa-prosta-5,10-dien-13-ynoic acid and its 15R-epimer.

We claim:
1. Compounds having general formulas (1)

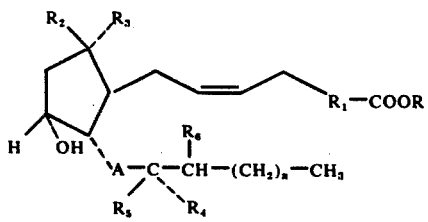 (1)

and (11)

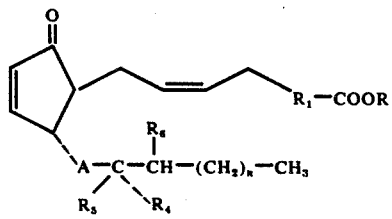 (11)

and the racemates thereof,
wherein R is a hydrogen atom, a pharmaceutically acceptable cation or a $C_{1-18}$ alkyl group or a trichloroethyl group; $R_1$ is —$CH_2CH_2$—, —$OCH_2$—, —$SCH_2$—, —CH=CH— or —C≡C—; one of $R_2$ and $R_3$ is a hydrogen atom and the other is a hydroxy group or $R_2$ and $R_3$ together form an oxo group; A is

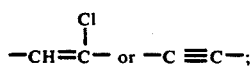 or —C≡C—;

one of $R_4$ and $R_5$ is a hydrogen atom and the other is a hydroxy group; $R_6$ is a hydrogen atom or a $C_{1-4}$ alkyl group; n is 3 or 4; and wherein the chains bound to the carbon atoms in the 8-position and in the 12-position have the trans-configuration.

2. 5c,13t-14-chloro-9α,11α,15S-trihydroxy-8,12-diiso-prostadienoic acid, as claimed in claim 1;

3. 5c,13t-14-chloro-9β,11α,15S-trihydroxy-8,12-diiso-prostadienoic acid, as claimed in claim 1;

4. 5c,13t-14-chloro-11α,15S-hydroxy-9-oxo-8,12-diiso-prostadienoic acid, as claimed in claim 1;

5. 5c,13t-14-chloro-15S-hydroxy-9-oxo-8,12-diiso-prosta-5,10,13-trienoic acid, as claimed in claim 1;

6. 5c-9α,11α,15S-trihydroxy-8,12-diiso-prosten-13-ynoic acid, as claimed in claim 1;

7. 5c-16-methyl-9α,11α,15S-trihydroxy-8,12-diiso-prosten-13-ynoic acid, as claimed in claim 1;

8. 5c-9α,11α,15S-trihydroxy-20ω-homo-8,12-diiso-prosten-13-ynoic acid, as claimed in claim 1;

9. 5c-9α,11α,15S-trihydroxy-3-oxa-8,12-diiso-prosten-13-ynoic acid, as claimed in claim 1;

10. 5c,9β,11α,15S-trihydroxy-8,12-diiso-prosten-13-ynoic acid, as claimed in claim 1;

11. 5c-11α,15S-dihydroxy-9-oxo-8,12-diiso-prosten-13-ynoic acid, as claimed in claim 1;

12. 5c-11α,15R-dihydroxy-9-oxo-8,12-diiso-prosten-13-ynoic acid, as claimed in claim 1;

13. 5c-16-methyl-11α,15S-dihydroxy-9-oxo-8,12-diiso-prosten-13-ynoic acid, as claimed in claim 1;

14. 5c-16-methyl-11α,15R-dihydroxy-9-oxo-8,12-diiso-prosten-13-ynoic acid, as claimed in claim 1;

15. 5c-11α,15S-dihydroxy-9-oxo-20ω-homo-8,12-diiso-prosten-13-ynoic acid, as claimed in claim 1;

16. 5c-11α,15R-dihydroxy-9-oxo-20ω-homo-8,12-diiso-prosten-13-ynoic acid, as claimed in claim 1;

17. 5c-11α,15S-dihydroxy-9-oxo-3-oxa-8,12-diiso-prosten-13-ynoic acid, as claimed in claim 1;

18. 5c-11α,15R-dihydroxy-9-oxo-3-oxa-8,12-diiso-prosten-13-ynoic acid, as claimed in claim 1;

19. 5c-15S-hydroxy-9-oxo-8,12-diiso-prosta-5,10-dien-13-ynoic acid, as claimed in claim 1;

20. 5c-16-methyl-15S-hydroxy-9-oxo-8,12-diiso-prosta-5,10-dien-13-ynoic acid, as claimed in claim 1;

21. 5c-15S-hydroxy-9-oxo-20ω-homo-8,12-diiso-prosta-5,10-dien-13-ynoic acid, as claimed in claim 1;

22. 5c-15S-hydroxy-9-oxo-3-oxa-8,12-diiso-prosta-5,10-dien-13-ynoic acid, as claimed in claim 1.

* * * * *